United States Patent [19]
Berne et al.

[11] Patent Number: 5,915,230
[45] Date of Patent: Jun. 22, 1999

[54] FAST METHODS FOR SIMULATING BIOMOLECULAR SYSTEMS WITH LONG-RANGE ELECTROSTATIC INTERACTIONS BY MOLECULAR DYNAMICS

[75] Inventors: Bruce J. Berne, Irvington; Ruhong Zhou, New York, both of N.Y.

[73] Assignee: The Trustees of Columbia University in the City of New York, New York, N.Y.

[21] Appl. No.: 08/754,306

[22] Filed: Nov. 21, 1996

Related U.S. Application Data

[60] Provisional application No. 60/007,414, Nov. 21, 1995.

[51] Int. Cl.[6] .............................. G06F 19/00; G06F 17/00
[52] U.S. Cl. ................................................ 702/22; 702/19
[58] Field of Search ...................... 364/496, 497, 364/499, 578; 436/86; 702/22, 19

[56] References Cited

PUBLICATIONS

Board, J.A. et al. (1992) *Chem. Phys. Lett.* 198(1,2):89–94 (Exhibit B).
Ding, Hong–Qiang et al. (1992) *J. Chem. Phys.* 97(6):4309–4315 (Exhibit C).
Greengard, L. (1988) The Rapid Evaluation of Potential Fields in Particle Systems, Preface (MIT Press, Cambridge) (Exhibit D).
Greengard, L. and Rokhlin, V. (1987) *J. Comp. Phys.* 73:325–348 (Exhibit E).
Humphreys, D.D. et al. (1994) *J. Phys. Chem.* 98(27):6885–6892 (Exhibit F).
Procacci, P. and Berne, B.J. (1994) *J. Chem. Phys.* 101(3):2421–2431.
Schmidt, K.E. and Lee, M.A. (1991) *J. Stat. Phys.* 63(5, 6):1223–1235 (Exhibit H).
Shimada, J. et al. (1994) *J. Comp Chem.* 15(1):28–43 (Exhibit I).
Tuckerman, M. et al. (1992) *J. Chem. Phys.* 97(3):1990–2001 (Exhibit J).
Watanabe, M. and Karplus, M. (1995) *J. Phys. Chem.* 99:5680–5697 (Exhibit K).
White, C.A. and Head–Gordon, M. (1994) *J. Chem. Phys.* 101(8):6593–6605 (Exhibit L).

*Primary Examiner*—Lila Feisee
*Assistant Examiner*—Nirmal S. Basi
*Attorney, Agent, or Firm*—John P. White; Cooper & Dunham LLP

[57] ABSTRACT

The invention provides a method for significantly speeding up the molecular dynamics simulation of large heterogeneous molecular assemblies in which there are a very large number of charged groups and in which there are strong and weak bonds. This method makes practicable the simulation of large protein solutions and thus can be used to simulate protein folding and the binding of substrates to protein molecules among other applications.

7 Claims, 10 Drawing Sheets

FAST METHODS FOR SIMULATING BIOMOLECULAR SYSTEMS WITH LONG-RANGE ELECTROSTATIC INTERACTIONS BY MOLECULAR DYNAMICS

This application claims the benefit of United States application Ser. No. 60/007,414, filed Nov. 21, 1995.

The invention disclosed herein was made with Government support under Grant No. GM 43340 from the National Institutes of Health and Grant No. SP 41RR06892 from the National Institute of Science Division of Research Resources. Accordingly, the U.S. Government has certain rights in this invention.

Throughout this application, various references are referred to by number within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

Molecular dynamics simulations of biological macromolecules [1, 2] are computationally demanding, owing to the large number of particles, as well as the complex nature of their associated interactions. There are generally two approaches to simplify this enormous computational problem: one is to use simpler physical models for the protein, the other is to develop more efficient theories or numerical methods without modification of the physical model. Focusing on the second approach, applicants have developed numerically more efficient methods to reduce the computational burden.

The most time-consuming part of the simulation is the calculation of the long-range pairwise Coulombic forces. The computational complexity for these Coulombic interactions scales as $O(N^2)$, where N is the number of particles, and O is the order. Since the interaction decays with distance as $O(r^{-1})$, it is normally not appropriate to use short cutoffs for electrostatic interactions, especially for large proteins where the long-range effects of inhomogeneous charge distributions are thought to be important [3, 4].

The second most time-consuming part of the simulation arises from the small time-steps required to accurately solve the equation of motion for the stiff bond stretch and bond bending vibrations, even though one may be primarily interested in events that occur over a much longer time scale. In standard numerical integration methods, such as those of the Stormer-Verlet variety [5, 6], one is generally required to use a time-step smaller than one femtosecond in order to maintain an acceptable level of accuracy in the integration of the equations of motion.

There have been a number of efforts to solve the first problem, i.e., to reduce the computational complexity for the electrostatic interactions. Hockney et al. [7] proposed a particle/mesh method to address this problem by using a mesh over the computational domain. The source density is interpolated at the mesh points, then the Poisson equation is solved to obtain the potential values on the mesh, and the forces are computed from the potential. The computational complexity is thus reduced from $O(N^2)$ to $O(NlogN)$. The mesh provides only limited resolution and highly nonuniform source distributions cause significant errors. To improve accuracy, a particle-particle/particle-mesh method was developed [8], in which the potential arising from short-range interactions is calculated directly. Appel [9] and Barnes et al. [10] developed a "tree code" method in place of the grid methods, in which the computational region is organized into a tree structure. The tree structure makes it possible to develop a rapid systematic procedure to determine which particles are "distant" from each other. By exploiting the fact that a particle interacts with a distant group of particles much as if it were interacting with a single particle at the center of mass (monopole) of the distant group, the complexity is also reduced to $O(NlogN)$, although there is again some loss of accuracy by using the monopole approximation.

Greengard and Rokhlin [11] developed the Fast Multipole Method (FMM) based on the "tree code" idea, but with higher order multipoles in addition to the simple monopole approximation. The FMM method first organizes multipole representations of charge distributions in hierarchically structured boxes, then transforms those multipoles into local field expansions, so that each particle interacts with the local field generated from distant particles. The multipoles are generated by direct calculation in the lowest level and successive shifting from lower levels to upper levels. This invention describes a top-down recursive method to generate the multipoles in the hierarchical box tree, in which the multipoles are calculated recursively from the top of the tree instead of from the bottom as in Greengard's FMM method. At each level of the tree, the method first looks for charged particles in every box. If there is no charged particles in a particular box, then the multipoles and local field expansions for that box and all its subdivided boxes are assigned automatically to be zero without any further calculations. This is more efficient for nonuniform or noncubic systems, such as proteins.

A variety of techniques have also been introduced to address the second problem, i.e. to increase the time-step in molecular dynamics (MD) simulations. One common approach is to constrain bond lengths using either the SHAKE or RATTLE methods [12, 13]. Although application of these methods allow for a modest increase in time-step, time dependent quantities may be affected [14, 15]. Additionally, the constraint methods have been shown to work poorly for bond angle degrees of freedom when applied to macromolecules [14].

Another approach to increase the time-step in MD simulations is that of the multiple time-step methods [16]. These methods are based upon integration schemes that allow for different time-steps according to how rapidly a given type of interaction is evolving in time. Teleman and Jönsson [17] introduced an method whereby the slower degrees of freedom are held constant for a number of smaller time-steps, which is usually called the long-range constant force approximation. This method has, however, been shown to lead to the accumulation of numerical error in calculated quantities [18, 19]. Alternatively, Swindoll and Haile [20] introduced a procedure which uses a Taylor series approximation for the less rapidly evolving forces. Although this method has been shown to give some improvement in central processing unit (CPU) times for simple systems such as alkane chain liquids [20], it is not yet evident whether it would be computationally advantageous in the case of macromolecules. This invention describes a multiple time-step method specifically for macromolecular simulation which uses a combination of time-steps of different lengths to integrate interactions which evolve on different time scales. The method is essentially a generalization of the reversible Reference System Propagation Approach (r-RESPA) [21], which employs a Trotter factorization [22] of the classical Liouville operator as a means to derive a numerical propagation scheme for the system. This r-RESPA scheme is a time reversible, symplectic (measure conserving in phase space), and highly stable integrator. This approach has been shown to be considerably more efficient than standard techniques when applied to simple systems or small proteins [19, 21, 23, 24].

SUMMARY OF THE INVENTION

The invention provides a method for significantly speeding up the molecular dynamics simulation of large heterogeneous molecular assemblies in which there are a very large number of charged groups and in which there are strong and weak bonds. This method makes practicable the simulation of large protein solutions and thus can be used to simulate protein folding and the binding of substrates to protein molecules among other applications.

The present invention is directed to a method of predicting the conformational changes that a molecule will undergo comprising the following steps:

(a) selecting a first conformation for the molecule characterized by a set of atoms, where each atom position is represented by a set of cartesian coordinates;

(b) sampling a set of initial velocities for the molecule from step (a) from a Maxwell distribution function;

(c) generating a hierarchical tree structure of nested boxes from top to bottom for the molecule, characterized by a multiplicity of subdivisions of a box containing the molecule of step (a);

(d) determining separately bond stretching, bond bending, torsional, and van der Waals forces associated with the molecule, the van der Waals forces being further characterized by distance separating interacting atoms;

(e) determining electrostatic forces for the molecule by:
(i) recursively generating a multipole representation of each charge distribution in each nonempty nested box at all levels of the hierarchical tree structure starting from the top of the hierarchical tree structure from step (c);
(ii) classifying the electrostatic interactions into groups of differing levels according to the distance over which they act;
(iii) determining the electrostatic forces acting upon each atom of the molecule by evaluating the force induced by the local expansion of the electric field associated with the multipoles generated in step (e)(i), wherein the level of the multipoles used is determined by the distance over which the interaction occurs as specified in step (e)(ii); and (f) propagating the molecule in time by:
(i) assigning different characteristic time steps for each class of forces specified in steps (d) and (e);
(ii) advancing both the position and the velocity for each of the atoms of the molecule from step (a) under the forces determined in steps (d) and (e), using a time-reversible factorization of a propagator which corresponds to Newton's equations of motion, wherein steps (d) and (e) are repeated after a simulation time proportional to the timestep prescribed in step (f)(i), thereby predicting the conformational changes that the molecule will undergo.

This dynamics approach leads to great reduction in the cpu time required for the calculation of forces and thus to dramatic speedup of the central processing unit (cpu) time for the molecular dynamics simulations of large biomolecules.

BRIEF DESCRIPTION OF THE FIGURES

FIG. 1A: The near zone—a lowest-level box (dotted box) and its 26 nearest neighbor boxes. FIG. 1B: The medium zone—its 98 2nd-nearest neighbor boxes (dashed boxes).

FIG. 3A: r-RESPA/TFMM vs the velocity Verlet. FIG. 3B: r-RESPA/TFMM vs the constant long-range force approximation (CLFA).

FIG. 4A: velocity Verlet with $\Delta t=0.25$ fs, FIG. 4B: velocity Verlet with $\Delta t=0.50$ fs, and FIG. 4C: r-RESPA/TFMM with time-step 4.0 fs (combination of (2,2,2,2) with $\delta t_1=0.25$ fs).

FIG. 6A: velocity Verlet with $\Delta t=0.25$ fs, FIG. 6B: velocity Verlet with $\Delta t=0.50$ fs, and FIG. 6C: r-RESPA/TFMM with time-step 4.0 fs (combination of (2,2,2,2) with $\delta t_1=0.25$ fs). Intensities are in arbitrary units.

FIG. 7A shows the spectral intensities for wave number 600–1700 (cm−1). FIG. 7B shows the spectral intensities for wave number 2850–3050 (cm−1). FIG. 7C shows the spectral intensities for wave number 3200–3500 (cm−1). FIG. 7D shows the spectral intensities for wave number 3700–3800 (cm−1).

DETAILED DESCRIPTION OF THE INVENTION

Figure 1A:
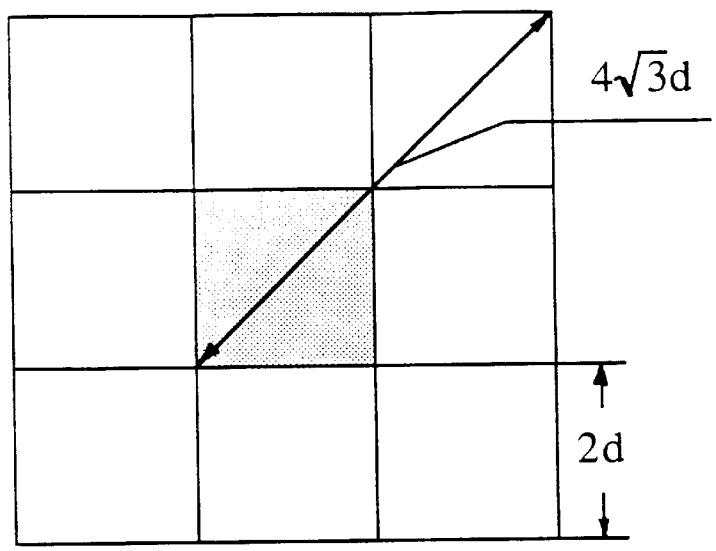
FIGS. 1A and 1B: A diagram showing the box separation for the electrostatic forces.

The invention provides a method for significantly speeding up the molecular dynamics simulation of large heterogeneous molecular assemblies in which there are a very large number of charged groups and in which there are strong and weak bonds. This method makes practicable the simulation of large protein solutions and thus can be used to simulate protein folding and the binding of substrates to protein molecules among other applications.

The method describe herein may be of particular use in rational drug design.

The present invention is directed to a method of predicting the conformational changes that a molecule will undergo comprising the following steps:
(a) selecting a first conformation for the molecule characterized by a set of atoms, wherein each atom position is represented by a set of Cartesian coordinates;
(b) sampling a set of initial velocities for the molecule from step (a) from a Maxwell distribution function;
(c) generating a hierarchical tree structure of nested boxes from top to bottom for the molecule, characterized by a multiplicity of subdivisions of a box containing the molecule of step (a);
(d) determining separately bond stretching, bond bending, torsional, and van der Waals forces associated with the molecule, the van der Waals forces being further characterized by distance separating interacting atoms;
(e) determining electrostatic forces for the molecule by:
(i) recursively generating a multipole representation of each charge distribution in each nonempty nested box at all levels of the hierarchical tree structure starting from the top of the hierarchical tree structure from step (c);
(ii) classifying the electrostatic interactions into groups of differing levels according to the distance over which they act;
(iii) determining the electrostatic forces acting upon each atom of the molecule by evaluating the force induced by the local expansion of the electric field associated with the multipoles generated in step (e)(i), wherein the level of the multipoles used is determined by the distance over which the interaction occurs as specified in step (e)(ii); and
(f) propagating the molecule in time by:
(i) assigning different characteristic time steps for each class of forces specified in steps (d) and (e)
(ii) advancing both the position and the velocity for each of the atoms of the molecule from step (a) under the forces determined in steps (d) and (e), using a time-reversible factorization of a propagator which corresponds to Newton's equations of motion, wherein steps (d) and (e) are repeated after a simulation time proportional to the timestep prescribed in step (f)(i), thereby predicting the conformational changes that the molecule will undergo.

The invention further provides for a method wherein one or more additional conformations of the molecule are generated by repeating step (f) of the method described above, thereby predicting the conformational changes that the molecule will undergo over time. The invention provides that the molecule may be a biomacromolecule or a macromolecule.

In particular the biomacromolecule may be a protein, wherein the Cartesian coordinates for the protein are obtained from a protein data base. In addition, the method provides that the molecule's nested boxes may be cubic or non-cubic. Furthermore the invention provides in one embodiment, the method wherein the molecule is surrounded by layers of solvent molecules and small solute molecules. For example solvent molecules include but are not limited to water and organic solvents. Examples of solute molecules include but are not limited to ions.

In one embodiment of the invention the conformational changes that a protein will undergo may be predicted from the following steps:
(a) Starting with the coordinates of a protein from a protein data base, a set of initial velocities are sampled from the Maxwell distribution function;
(b) a hierarchical tree structure of nested boxes is generated, characterized by a multiplicity of subdivisions of a large box containing the entire system which need not be cubic;
(c) determining separately the bond stretching, bond bending, torsional, and van der Waals forces associated with the system of step (a), the last of which is further classified according to the distance separating the interacting atoms;
(d) determining the electrostatic forces by using a new Top-Down Fast Multipole Method (TFMM), again classifying the interactions of length scale:
(i) recursively generating a multipole representation of the charge distribution in each nonempty box at all levels of the hierarchical structure prescribed in (b);
(ii) classifying the electrostatic interactions into several groups, depending on the distance over which they act;
(iii) approximating the electrostatic forces acting upon each atom of the system not through direct evaluation of atom-atom forces but by evaluating the force induced by the local expansion of the electric field associated with the charge distributions calculated in step (d)–(i), where the level of the charge distribution to be used is determined by the distance over which the interaction occurs, as specified in step (ii);
(e) propagating the system in time using the reversible Reference System Propagator Approach (r-RESPA):
(i) for each class of forces calculated in steps (c) and (d), assign different characteristic time steps;
(ii) advance both the positions and the velocities of the atoms in the system under the forces calculated in steps (c) and (d), through the use of a time-reversible factorization of the propagator corresponding to Newton's equations of motion in which each class of force described in steps (c) and (d) is recalculated after a simulation time proportional to the timestep prescribed in step (i);
(f) continuing to advance the system in time through repeated application of steps (b) through (e).

This approach leads to great reduction in the cpu time required for the calculation of forces and thus to dramatic speedup of the cpu time for the molecular dynamics simulations of large biomolecules.

The invention further provides a method of predicting the conformation which a molecule will assume, which comprises generating a series of conformations of the molecule using the method described herein, and then determining the lowest energy confirmation, thereby predicting the conformation which the molecule will assume. The invention provides that the molecule may be a biomolecule or a macromolecule. Specifically the biomolecule may be a protein or a protein with environments such as solvent molecules present.

The Fast Multipole Method

The Fast Multipole Method is an efficient method for evaluating Coulombic interactions between a large number of particles [11]. The CPU time increases linearly [O(N)] rather than as square of the number of particles [O($N^2$)]. This invention provides a method for multipole generation using a top-down recursive method based on White and Head-Gordon's simplified derivation [25].

FMM interpolates the potential and force on a particular charge due to distant charges not by direct calculation, but by using the local expansion of fields produced by the multipoles generated from those distant charges. Multipole representations of charge distributions are first organized in hierarchically structured boxes and then transformed into local field expansions. Each particle then interacts with the local field to count the interaction from distant particles. The short-range interactions are calculated directly. The potential consists of two parts:

$$\phi(\vec{x}) = \phi_{multipole}(\vec{x}) + \phi_{direct}(\vec{x}) \quad \text{(Equation 1)}$$

$\phi_{direct}$ contains the short-range inter-particle interactions and $\phi_{multipole}$ contains the contribution from distant particles.

FMM uses three parameters (n,p,ws): n represents the number of levels in the box tree, where the system is divided into $8^n$ lowest-level boxes; p is the number of terms used in the multipole expansions, ( e.g., p=2 includes contributions up to quadrupole, and p=4 includes contributions up to hexadecapoles ); ws is the parameter which defines well-separated boxes, where ws=1 indicates that $\phi_{direct}$ includes the contribution from the box itself and its 26 nearest-neighbor boxes, and ws=2 indicates $\phi_{direct}$ includes contributions up to the second nearest-neighbor boxes at the lowest-level in the tree. Box level 0 specifies the largest box which holds the whole system, while box level l+1 is obtained from level l by subdivision of each box into 8 smaller equal-sized boxes. A tree structure is then imposed on this box hierarchy. The 8 boxes at level l+1 obtained by subdivision of a box described as children, and the level l box is referred to as their parent box.

FMM method is based on the expansion of the Coulombic potentials in multipoles. For two unit charges at $r(r,\theta,\phi)$, and $a(a,\alpha,\beta)$ the potential may be written as $$\frac{1}{|r-a|} = \sum_{l=0}^{\infty} P_l(\cos\gamma) \frac{a^l}{r^{l+1}} \quad \text{(Equation No. 2)}$$

$$= \sum_{l=0}^{\infty} \sum_{m=-l}^{l} \frac{(l+m)!}{(l+m)!} \frac{a^l}{r^{l+1}} P_{lm}(\cos\alpha)$$

$$P_{lm}(\cos\theta)e^{-im(\beta-\phi)}$$

$$= \sum_{l=0}^{\infty} \sum_{m=-l}^{l} \frac{(l+|m|)!}{(l+|m|)!} \frac{a^l}{r^{l+1}} P_{l|m|}(\cos\alpha)$$

$$P_{l|m|}(\cos\theta)e^{-im(\beta-\phi)}$$

where y is the subtended angle between r and a (a<r).

The expansion separates the coordinates of the two particles in terms of associated Legendre polynomials. After redefining the associated Legendre polynomials [25], $$\tilde{P}_{lm} \equiv (l-m)! P_{lm} \quad \text{(Equation 3-a)}$$

$$\tilde{P}_{lm} \equiv \frac{1}{(l+m)!} P_{lm}, \quad \text{(Equation 3-b)}$$

the multipole moments and electric potentials can be expressed more compactly [25]. The moments of a multipole expansion about the origin (the box center) of a charge (or charge distribution) at a are defined as $$M_{lm}(a) = a^l \tilde{P}_{lm}(\cos\alpha)e^{-im\beta} \quad \text{(Equation No. 4-a)}$$

$$M_{lm}(q;a) = qM_{lm}(a) \quad \text{(Equation No. 4-b)}$$

$$M_{lm}(Q;A) = \Sigma M_{lm}(q;a), \quad \text{(Equation No. 4-c)}$$

where $M_{lm}(a)$ are the multipole moments about an origin (such as a box center) for a unit charge located at a with respect to that origin, $M_{lm}(q;a)$ are the multipole moments for a charge q at a, and $M_{lm}(Q;A)$ are the multipole moments for many charges in a box expanded around a common origin (box center). Capital letters denote collective sets of charges and positions in a box. Since these multipole moments $M_{lm}(Q;A)$ are all expanded with respect to the same origin, they can of course be summed directly. $M_{lm}$ is used for multipole moments and $L_{lm}$ for local field expansions (Taylor coefficients), which are different from White and HeadGordon's notation. Where $O_{lm}$ and $\mu_{lm}$ for multipole moments, and $M_{lm}$ and $\mu_{lm}$ for Taylor coefficients. The corresponding Taylor coefficients for a local field expansion of the potential due to a charge (or charge distribution) at r are then $$L_{lm}(r) = \frac{1}{r^{l+1}} \tilde{P}_{lm}(\cos\theta)e^{im\phi} \quad \text{(Equation No. 5-a)}$$

$$L_{lm}(q;r) = qL_{lm}(r) \quad \text{(Equation No. 5-b)}$$

$$L_{lm}(Q;r) = \Sigma L_{lm}(q;r) \quad \text{(Equation No. 5-c)}$$

where the indices have the same meaning as those in the multipole moments, except the charge is now located at r respect to the origin. Then the potential at r due a charge at a, or vice versa, could be expressed as $$\frac{q}{|r-a|} = \sum_{l=0}^{\infty} \sum_{m=-l}^{l} M_{lm}(q;a)L_{lm}(r) \quad \text{(Equation No. 6-a)}$$

$$= \sum_{l=0}^{\infty} \sum_{m=-l}^{l} M_{lm}(a)L_{lm}(q;r) \quad \text{(Equation No. 6-b)}$$

The expansion of above equation is exact in the limit of an infinite sum. However, it is normally not necessary to add up very high order multipoles or local expansions, and a truncation of p=3 or p=4 is usually sufficient for simulations which do not require extraordinarily high accuracies [11, 26]. The same level of truncation is appropriate for both the multipole and the local expansions.

FMM is used to build a hierarchical structure of multipoles, a tree structure, with each multipole containing the contribution of a subset of charges of limited spatial extent. The smallest box on the lowest level of the tree will then contain only a small number of particles (3–20). The boxes on successively higher levels (parent boxes) are the union of eight lower level children boxes, until one single box on the highest level contains all other boxes, and therefore all charges.

The multipoles associated with lowest level boxes are calculated according to equations 4(a)–4(c) directly. Multipoles of higher level boxes are calculated not from charges, but from the shifting of lower level multipoles. This is usually called an "upward pass", $$M_{lm}(Q; A+b) = \sum_{j=0}^{l} \sum_{k=-j}^{j} T_{lm,jk}^{MM}(b) M_{jk}(Q; A),$$ (Equation No. 7)

where b is the displacement of the multipole expansion center and the shift translation operator for multipole to multipole is shown in equation 8:

$$T_{lm,jk}^{MM}(b) = M_{l-j,m-k}(b)$$ (Equation No. 8).

A top-down recursive FMM is used which calculates multipoles recursively from the top of the tree instead of from the bottom as in "upward pass". It is a top-down recursive generation of the multipoles specially designed for biosystems, such as proteins, since these biomolecules are usually nonuniform and noncubic systems. By using the top-down generation scheme, it is easier to cut some "branch" of the tree if there are no charges in it. At each level in the recursive calculation, it first looks for charged particles in each box. If the number of charges in a box is zero then it skips all multipole calculations for the box, its children, grandchildren . . . , as well as all the corresponding local field translations described below. The top-down recursive calculation allows this pruning operation systematically, which is more efficient for noncubic or nonuniform systems.

Once multipoles $M_{lm}$ of all boxes are obtained, a local expansion $L_{lm}$ is constructed for each box, describing the potential inside the box caused by all distant charges $$L_{lm}(Q; A-b) = \sum_{j=0}^{\infty} \sum_{k=-j}^{j} T_{lm,jk}^{LM}(b) M_{jk}(Q; A)$$ (Equation No. 9)

and the transformation operator is $$T_{lm,jk}^{LM}(b) = L_{l-j,m-k}(b)$$ (Equation No. 10).

FMM uses higher-level local expansions efficiently in order to reduce the effort in subsequent transformations, since these transformations are the most CPU time consuming calculations in the FMM. The local expansions for a given level n are actually calculated using $$L_{lm}^{(n)} = L_{lm}'^{(n)} L_{lm}^{(n-1)},$$ (Equation No. 11)

where $L_{lm}'^{(n)}$ is the local expansions from the present contained in $L_{lm}^{(n-1)}$. For example, if there is a box $B_1$ at a given level, only the multipoles in boxes at this level which are well separated from $B_1$, but are not well-separated from $B_1$'s parent are transformed into local expansions in $B_1$. The number of these multipoles is never larger than $6^3-3^3=189$ for ws=1, and $10^3-5^3=875$ for ws=2.

The shift of a higher level expansion to a lower level is done much like the multipole shifts from a lower level to a higher level. This is usually called a "downward pass", $$L_{lm}(Q; R-b) = \sum_{j=l}^{\infty} \sum_{k=-j}^{j} T_{lm,jk}^{LL}(b) L_{jk}(Q; R),$$ (Equation No. 12)

and the shift translation operator from local expansion to local expansion is $$T_{lm,jk}^{LL}(b) = M_{j-l,k-m}(b).$$ (Equation No. 13)

Once the local expansions at the lowest level are known, the electrostatic potential and the forces are easily calculated by using Equations (1) and (6).

A top-down recursive FMM method is used to generate the multipole expansion, in an effort to be more efficient for noncubic or nonuniform systems, such as biosystems. Another way to save CPU time in the FMM is to use noncubic boxes to subdivide noncubic systems. Using noncubic boxes, such as rectangular boxes, may help to reduce the number of vacant boxes in the tree, and also reduce the number of pairs in neighbor boxes which need to be calculated directly. Thus, the CPU time required can be further reduced for noncubic systems. Care must be taken however when using noncubic boxes because the accuracy of the potential goes as $$\left|\Phi(r) - \frac{q}{|r-a|}\right| = |q| \sum_{l=p+1}^{\infty} P_l(\cos\gamma)\left(\frac{a}{r}\right)^{p+1} \leq$$ (Equation No. 14)

$$\frac{|q|}{r-a}\left(\frac{a}{r}\right)^{p+1},$$

where a refers to the positions for particles inside a lowest-level box, and r refers to the positions for particles in well-separated boxes. It is clear that the largest error will come from maximizing the ratio of a/r. For a lowest-level cubic box with side 2d, this maximum ratio occurs for a=3√d, and r=3d (for ws=2) or r=5d (for ws=2). Then, the error bound can be expressed as $$|\Phi_{exact} - \Phi_{ws=1}| \leq \frac{|q|}{(3-\sqrt{3})d}\left(\frac{1}{\sqrt{3}}\right)^{p+1}$$ (Equation No. 15-a)

$$|\Phi_{exact} - \Phi_{ws=2}| \leq \frac{|q|}{(5-\sqrt{3})d}\left(\frac{\sqrt{3}}{5}\right)^{p+1}.$$ (Equation No. 15-b)

However, if rectangular boxes are used with sides $d_1 \leq d_2 \leq d_3$, $a=\sqrt{3d}$ should now be replaced by $a=(d_1+d_2+d_3)$, and $r=3d$ $(r=5d)$ should be replaced by $r=3d_1$ $(r=5d_1)$ ($d_1$ is the smallest dimension in $d_1$, $d_2$, and $d_3$ for a rectangular box). If $d_1$ is much less than other two dimensions, for example in linear molecules like some polymers, the accuracy may go down when higher p is used, because a may be larger than r in some particular cases. So for these linear molecules, it may not be appropriate to use noncubic boxes. One way to solve this problem may be to use several adjoining level 0 boxes to hold the whole molecule, instead of using only one level 0 box. The top-down recursive method is also useful for these linear molecules.

Since the three dimensions for most proteins are normally comparable (the difference is less than a factor of three for all proteins studied), and also since we do not require very high p, noncubic boxes could be used to divide protein molecules, with a little loss of accuracy. Thus both the top-down recursive method and noncubic boxes are used in the following simulations (referred to hereinafter as "TFMM").

The Reversible Reference System Propagator Approach the Trotter Expansion of the Liouville Propagator The Reference System Propagator Approach (RESPA) for molecular dynamics was first introduced by Tuckerman, Martyna, Berne [18, 21]. It has been shown to be much more efficient than standard techniques, such as the velocity Verlet method. The early applications were applied to simple systems with stiff and soft forces, shorthand long-range interactions, and disparate masses [21, 27]. Recently, this approach has been successfully applied to diatomic molecules in solution [28], small organic molecules by Watanabe and Karplus [23], the fullerene crystal by Procacci and Berne [24], and a small protein by Humphreys and Berne [19].

The reversible RESPA [27] is based upon the Trotter expansion of the classical Liouville propagator. The Liouville operator, L, for a system of N degrees of freedom in Cartesian coordinates is defined as $$iL = [\ldots, H] = \sum_{i=1}^{N}\left[\dot{x}_i \frac{\partial}{\partial x_i} + F_i(x)\frac{\partial}{\partial p_i}\right],$$ (Equation No. 16)

where $[\ldots, \ldots]$ is the Poisson bracket, H is the Hamiltonian, $(x_i, p_i)$ is the position and conjugate momentum for the coordinate i. The state of the system at a time t, $\Gamma(t)$, is defined as the collective set of positions and conjugate momenta $\{x(t), p(t)\}$. It evolves with time as $$\Gamma(t) = U_{(t)}\Gamma_{(0)},$$ (Equation No. 17)

where U(t) is the classical time evolution propagator $$U_{(t)} = e^{itL}.$$ (Equation No. 18)

Since the classical Liouville operator is self-adjoint, U(t) is a unitary operator and the time evolution in above equation is reversible.

The Liouville operator is then decomposed into two parts, such that $$L = L_1 + L_2.$$ (Equation 19)

This allows the Trotter theorem to be applied [22] giving $$e^{i(L_1+L_2)t} = e^{i[\Delta t(L_1+L_2)]^N}$$ (Equation No. 20)

$$= ([e^{i(\Delta t/2)L_2} e^{i\Delta t L_1} e^{i(\Delta t/2)L_2}])^N + O(\Delta t^3),$$

where $\Delta t \equiv t/N$. In practice, $\Delta t$ is chosen small enough, i.e. N large enough, to generate an accurate and stable MD simulation. A discrete time propagator may then be defined as $$G(\Delta t) = U_2(\Delta t/2)U_1(\Delta t)U_2(\Delta t/2)$$ (Equation No. 21)

$$= e^{i(\Delta t/2)L_2} e^{i\Delta t L_1} e^{i(\Delta t/2)L_2}.$$

The inner propagator in Equation No. 21 can be further decomposed as $$e^{i\Delta t L_2} = ([e^{i\delta \tau L_1}])^n$$ (Equation No. 22)

$$= \left(\left[e^{(\delta \tau_1/2)F_1(x)\frac{\partial}{\partial p}} e^{\delta \tau_1 \dot{x}\frac{\partial}{\partial x}} e^{(\delta \tau_1/2)F_1(x)\frac{\partial}{\partial p}}\right]\right)^n +$$

$$O(\delta \tau_1^3),$$

if $$L_1 = \dot{x}\frac{\partial}{\partial x} + F_1(x)\frac{\partial}{\partial p}$$

This provides a means for determining the time evolution of a system whose interactions evolve according to two different time scales. That is, the inner propagator $e^{i\Delta t L_1}$ may be taken to be associated with the rapidly varying interactions with a smaller time-step, which we call a "reference" system propagator. The outer propagators are used to evolve the slowly varying interactions with a larger time-step, which has been named a "correction" propagator. The formal solution for the discretized equations of motion is then given by $$\Gamma(\Delta t) = U_2(\Delta t/2)U_1(\Delta t)U_2(\Delta t/2)\Gamma(0) +$$ (Equation No. 23)

$$O(\Delta t^3)$$

$$= e^{i(n\delta\tau/2)L_2}[e^{i\delta\tau L_1}]^n e^{i(n\delta\tau/2)L_2}\Gamma(0) +$$

$$O(\Delta t^3).$$

This approach can be easily expanded to a general case with more than two effective time scales. If there are m different time scales for a particular system, so the Liouville operator is broken down into a sum of m terms, $$L = L_1 + L_2 + \ldots + L_m.$$ (Equation No. 24)

It follows that the entire discretized propagator for a system with m time-scales can be written as $$G(\Delta t) \equiv e^{i(n_1 n_2 \ldots n_{m-1}\delta\tau_1/2)L_m} \ldots \times$$ (Equation No. 25)

$$[e^{i(n_1\delta\tau_1/2)L_2}[e^{i\delta\tau_1 L_1}]^{n_1} e^{i(n_1\delta\tau_1/2)L_2}]^{n_2} \ldots$$

$$\times e^{i(n_1 n_2 \ldots n_{m-1}\delta\tau_1/2)L_m}.$$

The m different timescales are given by $$\delta\tau_1, n_1\delta\xi_1, n_1n_2\delta\tau_1, \ldots, n_1n_2 \ldots n_{m-1}\delta\tau_1.$$

This corresponds to a situation where the innermost reference propagator is evaluated every small time-step $\delta\tau_1$, the 2nd innermost correction propagator is evaluated every $n_1$ small steps, and so on, with the mth correction propagator evaluated only every $n_1, n_2 \ldots n_{m-1}$ small time-steps.

Reversible Reference System Propagation Approach (r-RESPA) for Biomolecules

In order to apply the techniques discussed above to the molecular dynamics (MD) simulation of biomolecules, the Liouville operator for a macromolecule in vacuo containing N atoms is $$iL = \sum_{i}^{3N}\left[\dot{x}_i \frac{\partial}{\partial x_i} + F_i(x)\frac{\partial}{\partial p_i}\right],$$ (Equation No. 26)

where $$F(x) = F_{stret}(x) + F_{bend}(x) + F_{tors}(x) + F_{Hbond}(x) +$$
$$F_{vdW}(x) + F_{elc}(x),$$ (Equation No. 27)

$F_{stret}$, $F_{bend}$, $F_{tors}$, $F_{hbond}$, $F_{vdW}$, $F_{elec}$ represent the forces for stretch, bending, torsion (including improper torsion), hydrogen-bonding, van der Waals, and electrostatic interactions, respectively. Their functional forms can be found elsewhere [29, 30]. The databases of parameters for these functional forms are generally called force fields. There are several force fields available for biomolecular simulations, such as CHARMM [3], AMBER [30], OPLS [31] etc.

In an atomic level simulation using force fields, the stretch vibrations are usually the fastest motions in the molecular dynamics of biomolecules, and the evolution of the stretch vibration as a "reference" propagator with the smallest time scale is used. The nonbonded interaction, including van der Waals and electrostatic forces, are the slowest varying interactions, and a much larger time-step may be used. The bending, torsion and hydrogen-bonding forces are treated as intermediate time-scale interactions.

In addition, the nonbonded forces can be divided into several regions in pair distance according to their importance and varying speeds. The near region is normally more important than the distant region because the nonbonded forces decay with distance. Since most of the central processing unit (CPU) time in a MD simulation is spent in the calculation of these nonbonded interactions, the separation in pair distance results in valuable speedups.

Using a 3-fold distance split, the nonbonded forces are separated in 3 regions: near, medium (med), and far distance zones. Thus, the Liouville operator can be express as a sum of five terms $$L = L_1 + L_2 + L_3 + L_4 + L_5, \quad \text{(Equation No. 28)}$$

where $$iL_1 \equiv \dot{x}\frac{\partial}{\partial x} + F_1(x)\frac{\partial}{\partial p} \quad \text{(Equation No. 29-a)}$$

$$iL_i \equiv F_i(x)\frac{\partial}{\partial p}, \quad i = 2, 3, 4, 5 \quad \text{(Equation No. 29-b)}$$

and $$F_1(x) (\equiv F_{stret}(x)) \quad \text{(Equation No. 30-a)}$$

$$F_2(x) \equiv F_{bend}(x) + F_{tors}(x) + F_{Hbond}(x) \quad \text{(Equation No. 30-b)}$$

$$F_3(x) \equiv F_{vdW}^{near}(x) + F_{elec}^{near}(x) \quad \text{(Equation No. 30-c)}$$

$$F_4(x) \equiv F_{vdW}^{med}(x) + F_{elec}^{med}(x) \quad \text{(Equation No. 30-d)}$$

$$F_5(x) \equiv F_{vdW}^{far}(x) + F_{elec}^{far}(x) \quad \text{(Equation No. 30-e)}$$

To separate the nonbonded forces into near, medium, and far zones, pair distance separations are used for the van der Waals forces, and box separations are used for the electrostatic forces since the box separation is a more convenient breakup in the TFMM method.

The distance separation for van der Waals forces is most easily implemented by using switching functions [21, 27]. For example, to separate the pairwise interaction $F_{vdW}$ into m subsegments in the pair distance regions, i.e. $[0-r_1]$, $[r_1-r_2]$, ..., and $[r_{m-1}-r_m]$, the van der Waals force may be written as $$F_{vdW}(x) = \sum_{k=1}^{m} F_{vdW}^k(x) \equiv \sum_{k=1}^{m} [S_k(r) - S_{k-1}(r)] F_{vdW}(x) \quad \text{(Equation No. 31)}$$

where $S_k(r)$ are switching functions which are defined as $$S_0(r) \equiv 0; S_m(r) \equiv 1.0 \quad \text{(Equation No. 32)}$$

and

-continued $$S_k(r) = \begin{cases} 1, & 0 \le r < r_k - \Delta r_k \\ 1 - R_k^2(3 - 2R_k), & r_k - \Delta r_k \le r \le r_k \\ 0, & r_k \le r. \end{cases}$$

Here, $$R_k \equiv [r - (r_k - \Delta r_k)]/\Delta r_k,$$

and r is the interatomic distance, $r_k$ is the kth distance cutoff, and $\Delta r_k$ is the kth healing length. The analytical form for the switching function is arbitrary, and the only requirement is that it and its first derivative are to be continuous, at $r_k$ and $r_k - \Delta r_k$. The reason to use switching functions is to avoid the sudden changes in forces when crossing between different distance regions. This ensures that the force in the first region ($0 < r \le r_1$) decreases smoothly to zero at $r_1$, and in other regions, such as in the kth region, it increases smoothly from zero at $r_{k-1}$ and decreases smoothly to zero at $r_k$. Using this method, highly stable molecular dynamics simulations are possible.

The box separation used for the electrostatic interactions is taken to be consistent with the box division in the TFMM. For a particular box in the lowest-level, the box and its 26 nearest boxes are regarded as the near zone, its 98 ($5^3 - 3^3$) 2nd-nearest neighbor boxes as the medium zone, and all the other boxes as the far zone. Using ws=2 in the TFMM is even faster than ws=1 if a high accuracy level is required. Thus, for the box separation of the electrostatic forces, using ws=2 may be a better choice than using ws=1, since it is more convenient to calculate the forces from near and medium zones directly, and forces from the far zone by local field expansions from distant multipoles, which is exactly what is done in the TFMM with ws=2.

Figure 1B:
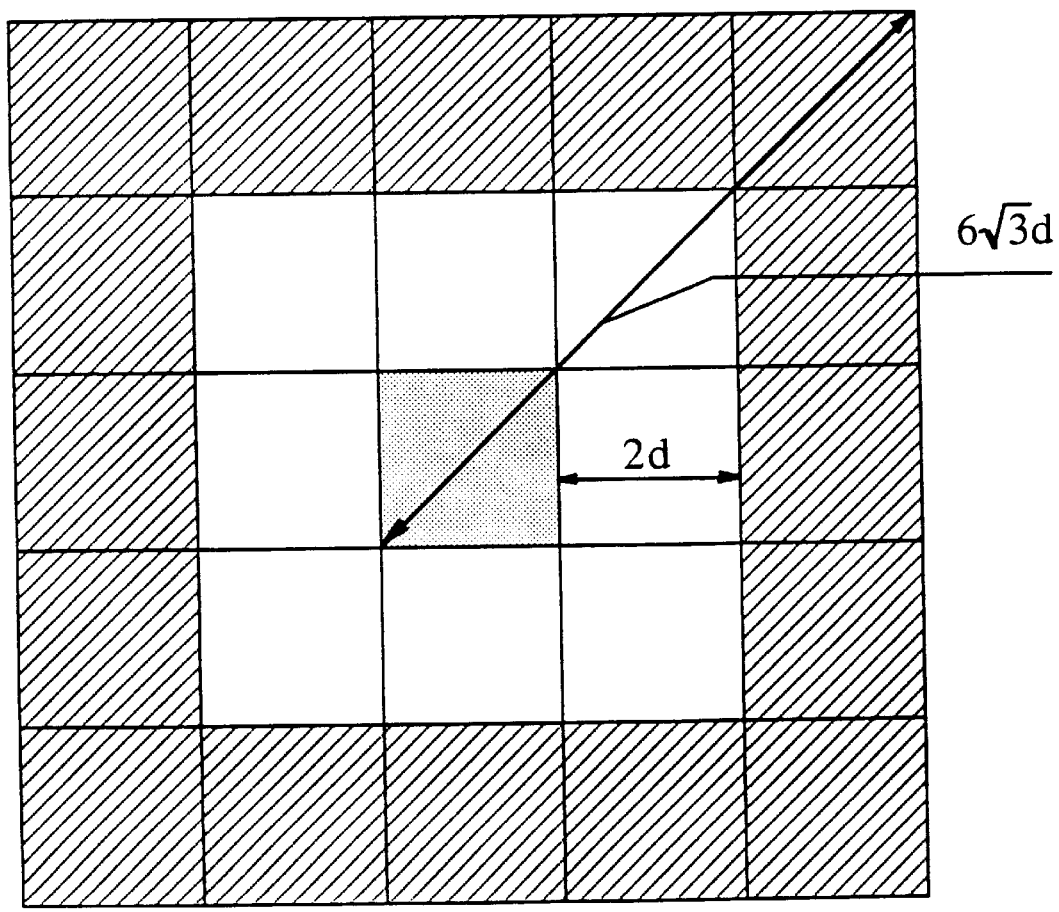

A diagram for the near and medium zones for the electrostatic forces is given in FIG. 1. Cubic boxes were used for simplicity. Assuming that the side-length for the smallest box in the tree is 2d, the pair distance in the near zone, as shown in FIG. 1A, ranges from 0 to $4\sqrt{3}d$; the medium zone, as shown in FIG. 1B, ranges from 2d to $6\sqrt{3}d$; and the far zone ranges from 4d to infinity. Since these zones are constructed from cubic boxes, they are not spherical shells, therefore these zones overlap in distance. The overlap region will be wider if rectangular boxes are used. The pair numbers in the overlap region decrease to zero slowly for the nearer zone since there are few pairs of atoms which are in opposing corners, and increase slowly from a small number for the next zone for a similar reason. For example, in the overlap region ($2d - 4\sqrt{3}d$) of the near and medium zones, the pair numbers for the near zone decreases slowly to zero when the pair distance goes to $4\sqrt{32}d$, and the pair numbers for the medium zone increases slowly from a small number when the distance increases from 2d. This means that the pair numbers in the overlap regions behave as a sort of switching function, so that no explicit switching functions are used for the electrostatic forces. The MD simulations presented show that very stable MD simulations can be generated using this box separation for electrostatic forces without an explicit switching function.

After separating the nonbonded forces in the three distance regions, one may write the discretized propagator as $$G(\Delta t) \equiv e^{i(n_1 n_2 n_3 n_4 \delta\tau_1/2)L_5} [e^{i(n_1 n_2 n_3 \delta\tau_1/2)L_4} \times$$

$$([e^{i(n_1 n_2 \delta\tau_1/2)L_3} [e^{i(n_1 \delta\tau_1/2)L_2} [e^{i\delta\tau_1 L_1}]^{n_1} e^{i(n_1 \delta\tau_1/2)L_2}]^{n_2} e^{i(n_1 n_2 \delta\tau_1/2)L_3}]^{n_3} \times e^{i(n_1 n_2 n_3 \delta\tau_1/2)L_4}]^{n_4} e^{i(n_1 n_2 n_3 n_4 \delta\tau_1/2)L_5} ,$$

(Equation No. 33)

where $L_1$, $L_2$, $L_3$, $L_4$ and $L_5$ are given by Equations No. 29-a and 29-b. The inner "reference" propagator in Equation No. 33, which contains the bond stretching vibrations evolution, is given by $$e^{i\delta\tau_1 L_1} = e^{\delta\tau_1 \left(\dot{x}\frac{\partial}{\partial x} + F_1(x)\frac{\partial}{\partial p}\right)}.$$

(Equation No. 34)

This can be further expanded by using the following Trotter factorization $$e^{\delta\tau_1 \left(\dot{x}\frac{\partial}{\partial x} + F_1(x)\frac{\partial}{\partial p}\right)} = e^{(\delta\tau_1/2)F_1(x)\frac{\partial}{\partial p}} e^{\delta\tau_1 \dot{x}\frac{\partial}{\partial x}} e^{(\delta\tau_1/2)F_1(x)\frac{\partial}{\partial p}} + O(\delta\tau_1^3).$$

(Equation No. 35)

This factorization is equivalent to the velocity Verlet approach [21, 27]. The outer "correction" propagators $e^{(i\delta\tau_m/2)L^m}$, for m=2, 3, 4, 5, are of the form $$e^{(\delta\tau_m/2)F_m(x)\frac{\partial}{\partial p}}.$$

(Equation No. 36)

After acting to the right on an arbitrary state $\{x,p\}$, $$e^{(\delta\tau_m/2)F_m(x)\frac{\partial}{\partial p}}\{x, p\} = \{x, p + (\delta\tau_m/2)F_m(x)\}.$$

(Equation No. 37)

Thus, the evolution of the system is determined numerically by acting with the propagator in Equation No. 33 to the right on the initial state $\{x(0),p(0)\}$, using Equation No. 37 and Equation No. 35.

The new MD method based on the combination of TFMM and r-RESPA was applied to simulations of proteins in vacuo. The TFMM was used to calculate electrostatic interactions for large protein molecules and the propagator in Equation No. 33 was used to generate the integration scheme, with a reference propagator of the form in Equation No. 35.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Computational Implementation

The potential parameters used are adopted from the AMBER [30] force field, although the program is designed to be capable of using various force fields. The full long-range Coulomb potentials ($O(r^{-1})$) were used in the simulation by taking advantage of the fast multipole method. For the short-range van der Waals potentials ($O(r^{-6})$), a cutoff distance of $r_c=12$ Å was used. The cutoff was made such that the forces and their first derivatives go smoothly to zero at $r_c$ by using a switching function as in Equation No. 32. The calculation results show that $r_c=12$ Å is large enough for the van der Waals potentials.

Normally, molecular simulations using force fields exclude nonbonding forces between atoms that are considered to be chemically bonded. It is more convenient to calculate potentials and forces for all point charges in the FMM, the chemically bonded pair contributions from the FMM results need to be subtracted. Usually, (1,2) stretching and (1,3) bending interactions are excluded totally in all force fields, but (1,4) torsional interactions are treated slightly differently in various force fields due to different choices of parameters. In the AMBER force field, only ½ of the (1,4) interactions are subtracted.

The FMM method was implemented as a portable module using the C programming language. It uses a tree structure of boxes to handle the multipoles and Taylor expansions. For example, a specific box in the tree can be described as "box[n][i][j][k]" in C language syntax, where n is the level in the tree, and i, j, k are indices of the box in x, y, and z directions respectively, which can range from 0 to $2^n$. The eight nearest neighbors can be easily accessed by i'=i+{1, 0,-1}; j'=j+{1,0,-1}; and k'=k+{1,0,-1}. Furthermore, its parent is now just box [n-1][i/2][j/2][k/2], and its eight children are given by box [n+1][2i+{0,1}][2j+{0,1}][2k+{0,1}]. All the multipoles and Taylor expansions can be well organized through this structure for use in the "upward" and "downward" passes. In the top-down FMM, the charges in each box[n][i][j][k] are first checked during the recursive multipole calculation from the top of tree. If the charge is zero, then the multipole and corresponding Taylor expansion coefficients for this box and all its children and grandchildren are assigned to be zero without any further calculations.

The FMM module is then called by a MD module which is written in FORTRAN. The implementation of the r-RESPA approach in the MD module is straightforward, and a schematic FORTRAN code can be found elsewhere [19]. All simulations were performed on IBM RISC6000/ model 580 and 590 computers.

Protein Simulations

Six protein systems in vacuo were used in simulations using the MD method: a 292-atom fraction of insulin (4insb), crambin (655 atoms, lcrn), interleukin 8 (1144 atoms, 3i18), ribonuclease-H (2470 atoms, 2rn2), L-*arabinose-Binding Protein (4674 atoms, 8abp), and the Photosynthetic Reaction Center (including the active branch, only subunit L and subunit C, 9513 atoms, lprc).

Before performing a production MD simulation, some primary "treatments" were applied to the initial X-ray structure from Brookhaven Protein Data Base file (Brookhaven National Laboratory, Upton, N.Y.; World Wide Web HTTP-:WWW.CCD.BNL.GOV; additional protein data base structures may be obtained from the Cambridge Data Base, Cambridge University, England), with the addition of explicit H atoms. First, the X-ray structure was minimized using the conjugate gradient method to obtain a minimum energy structure. This is necessary because AMBER and other available force fields, while reasonable, are not sufficiently accurate to give exact structures, and the explicit H atoms added by the program may not be in correct positions. Typically, it takes several thousand iterations to minimize a 1000-atom protein, and tens of thousands of iterations to minimize a 5000-atom protein. The RMS deviation for the minimized structure compared to the initial X-ray structure is usually very small, only 0.5 Å–1.0 Å. The initial velocities are then sampled from a Maxwell-Boltzmann distribution at a given initial temperature, such as 100K. In order to avoid having the structure blow up, the minimized structure is slowly heated up to 300K from 100K over a 10 ps MD run. This is then followed by a 20 picosecond (ps) molecular dynamics (MD) run at 300K (canonical ensemble) for equilibration. During the equilibration the velocities are resampled from a Maxwell-Boltzmann distribution periodically if the average temperature over the previous 0.5 ps deviates from 300K by more than ±5K.

Optimum Parameters for TFMM

Three parameters (n, p, ws) are used in the FMM. The optimum values for these parameters were determined for the molecular dynamics simulation.

The total number of tree levels n was determined by $$n = int\left(\log_8 \frac{N}{N_0}\right) \quad \text{(Equation No. 38)}$$

where the int function returns the integer part, N is the number of total atoms, and $N_0$ is the desired average particle number in the finnest-level box. Generally, using a larger $N_0$ requires more multipole terms to obtain a given level of accuracy, and thus more CPU time; however, using a smaller $N_0$ may result in more tree levels, and thus more CPU overheads in FMM as well. Various simulations have shown that setting $N_0$ to 2–16 is an optimum choice [11, 25, 26, 32] and similar settings are determined by calculation. The optimum tree level n and the average particle number in the finnest-level box $N_0$ for various proteins are listed in Table 1.

For the well-separated parameter ws, when ws=1 it is faster but less accurate than ws=2 for the same p level. Thus, which is more efficient for a given level of accuracy: to use ws=1 with a higher p or use ws=2 with a lower p, needs to be determined. Two measures of accuracy need to be defined, (1) the relative error in the potential and (2) the relative error in the forces:

$$\Delta\Phi = \frac{|\Phi_{direct} - \Phi_{TFMM}|}{|\Phi_{direct}|} \quad \text{(Equation 39-a)}$$

$$\Delta F = \frac{|F^{(i)}_{direct} - F^{(i)}_{TFMM}|^2}{\sum |F^{(i)}_{direct}|^2}. \quad \text{(Equation 39-b)}$$

Numerical results for ws=1 and ws=2 are listed in Table 2. For ws=1, ΔF is $10^{-2}$–$10^{-3}$ for p=4; while for ws=2, ΔF is about $10^{-3}$ to $-10^{-4}$ for p=4. Thus, ws=2 is approximately ten times as accurate as ws=1. To reach the same accuracy as that in ws=2 with p=4, multipoles up to p=8 should be used in ws=1, which requires more CPU time. This was consistent with Greengard [11] and Head-Gordon [25] where it was found that ws=2 was the optimum choice. The crossover point for the TFMM vs direct evaluation (Table 2) was about 1000 atoms for ws=2 at an accuracy level of ΔΦ ~$10^{-4}$–$10^{-5}$ and ΔF ~$10^{-3}$–$10^{-4}$, which is comparable or even better than previously reported [11, 25, 26, 32].

In addition, since distance separations may be used in the r-RESPA approach, ws=2 was a better choice for MD simulations because the nearest neighbor boxes can be used as the near zone, the 2nd-nearest shell of box as the medium zone, and all the other boxes as the far zone.

The p level sufficient to generate a stable MD simulation was determined, i.e., to avoid possible accumulation of errors in MD runs. Two energy conservation parameters are commonly used to describe the stability of a constant-energy MD simulation [19, 23]. First, the total energy fluctuation ΔE defined by $$\Delta E \equiv \frac{1}{N_T} \sum_{i=1}^{N_T} \left|\frac{E_{initial} - E_i}{E_{initial}}\right|, \quad \text{(Equation No. 40)}$$

where $E_i$ is the total energy at step i, $E_{initial}$ is the initial energy, and $N_T$ is the total number of time-steps. This quantity has been shown to be a reasonable measure of accuracy in previous simulations [19, 23], and a value of ΔE≦0.003, i.e., log (ΔE)≦2.5, gives an acceptable numerical accuracy. A second common measure of the accuracy is the ratio of the RMS deviation of the total energy to the RMS deviation of the kinetic energy [33], $$R \equiv \frac{\Delta E_{rms}}{\Delta KE_{rms}}. \quad \text{(Equation No. 41)}$$

A value of R≦0.05, can be used as an alternate criterion for stability in MD simulations [19, 23].

Figure 2:
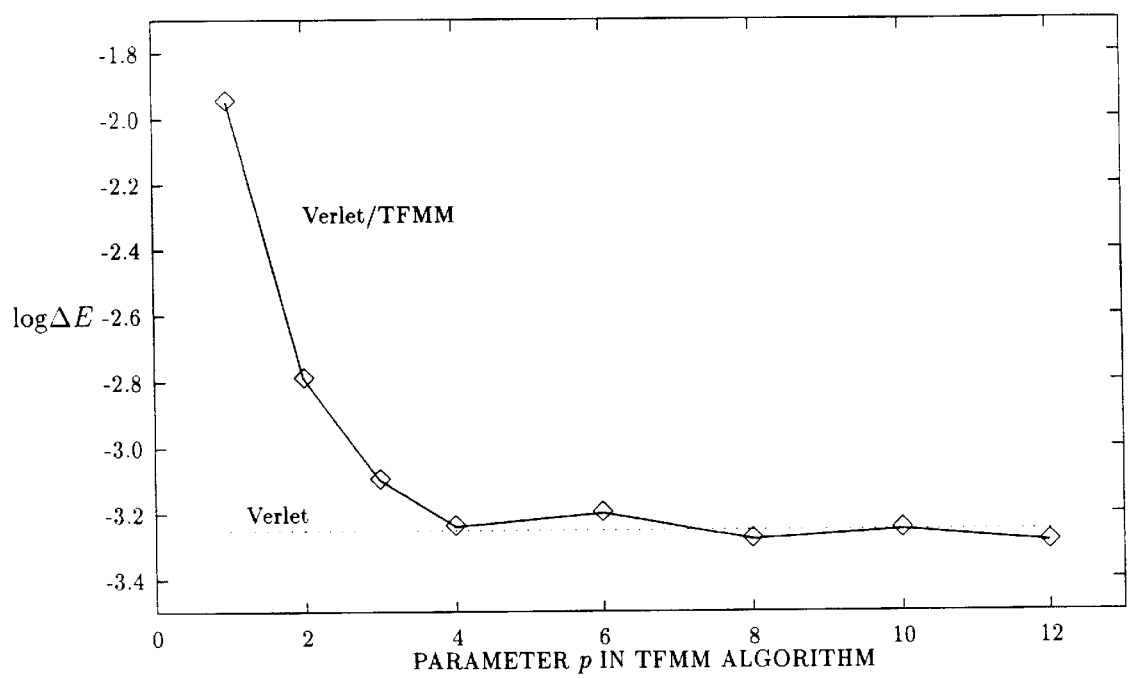
FIG. 2: Dependence of energy conservation on the parameter, p, used in the FMM method which is now incorporated in MD module, (p=2, includes contributions up to quadrupole, p=4, to hexadecapoles).

The protein ribonuclease-H (2rn2) is used as an example to perform constant energy (micro-canonical ensemble) MD simulations to determine the necessary p level. FIG. 2 shows the dependence of log(ΔE) versus p for 1 ps MD simulation using the standard velocity Verlet integration scheme with the new version of FMM implemented for Coulomb forces. The result for the direct electrostatic calculation is also included for comparison. It was found that p=4, which includes contributions up to hexadecapoles, is sufficient for a stable constant-energy MD simulation. So in the following simulations, p=4 was used.

The three parameters used in TFMM have been optimized for the MD simulation. The tree levels n for various proteins are listed in Table 1 ($N_0$ equals to 2–10). The other two parameters are set to p=4 and ws=2 for all proteins studied.

Energy Conservation Comparison

The energy conservation for three different methods, r-RESPA, velocity Verlet, and Constant Long-range Force Approximation (CLFA) were compared.

In r-RESPA, forces are separated according to their intrinsically different time scales to increase the overall time-step. The notations, $n_1$, $n_2$, $n_3$, $n_4$, were used to indicate different combinations of timescale separation. That is, if the time-step is δt for stretching forces, then the time-step is $n_1 \delta t$ for bending, torsion and H-bond forces, $n_1 n_2 \delta t$ for near zone van der Waals and electrostatic forces, $n_1 n_2 n_3 \delta t$ for medium zone van der Waals and electrostatic forces, $n_1 n_2 n_3 n_4 \delta t$ for far zone van der Waals and electrostatic forces.

The near, medium, and far zones are divided using pair distance separations for van der Waals forces and box separations for electrostatic forces. A good choice for the near zone in dividing the van der Waals forces using a switching function is $r_1$=7–9 Å (with healing length of 1.5–2.0 Å). A value of $r_1$=8.0 Å is used in the following simulations. The pair distance region (8 Å–12 Å) was defined as the medium zone, and no far zone of van der Waals forces is actually included here because of the cutoff at 12.0 Å, which is sufficiently large for van der Waals forces.

Box separation for the electrostatic forces is more convenient within the FMM (ws=2 is used). For simplicity, a cubic-box subdivision is considered. The side-length (2d) for the smallest box in the tree, which contains 2 to 10 atoms on average, is from 4 Å to 6 Å for all proteins studied, i.e. d=2.0 to 3.0 Å. Using an average value of d=2.5 Å for estimation, the pair distance for the electrostatic near zone, which includes the smallest box and its 26 nearest neighbor boxes, ranges from 0 to $4\sqrt{3}d$ (0 to 17.3 Å). The medium zone encompasses the 2nd nearest neighbor boxes, ranging from 2d to $6\sqrt{3}d$ (5.0 to 26.0 Å), and the far zone from 4d to infinity ($\leq 10.0$ Å). The electrostatic forces in the near and medium zones are evaluated directly, while the contributions from the far zone are evaluated by local field expansions from distant multipoles. No explicit switching functions are used for electrostatic forces since these zones overlap in distance and the pair numbers in the overlap region behave as a sort of switching function.

Physically, the separation of nonbonded forces on the basis of the pair distance is a "short/long" range breakup, the separation of bonded forces from nonbonded forces is an "internal/external" force breakup, and the separation of stretching vibrations from other bonded interactions is a "stiff/soft" force breakup. These three separations have been shown to be ideal for the application of the r-RESPA method [27, 28]. It is the difference in intrinsic time scales in these breakups that makes the r-RESPA approach valuable and powerful.

Figure 3A:
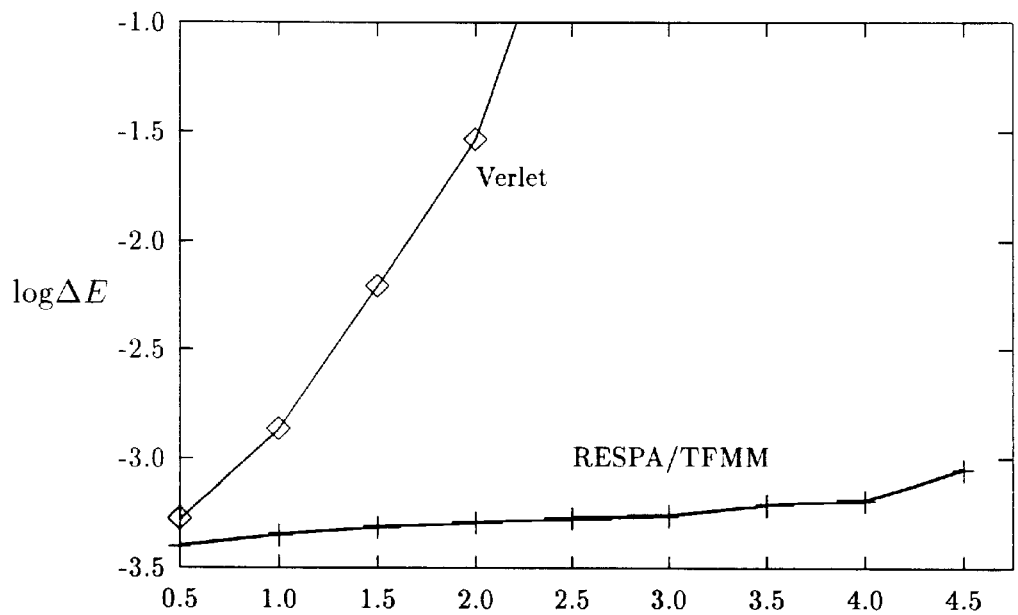
FIGS. 3A and 3B: Comparison of the energy conservation for various methods in a 1 picosecond (ps) constant-energy MD runs for the protein ribonuclease-H.

FIG. 3A shows the energy conservation performances of velocity Verlet and rRESPA/TFMM. The protein ribonuclease-H was studied, with 1 ps MD runs for both methods. The curve for r-RESPA/TFMM is obtained from various combinations of ($n_1$, $n_2$, $n_3$, $n_4$) with the smallest time-step of $\delta t$=0.25 fs. The overall time-step is then given by $\Delta t = n_1 n_2 n_3 n_4 \delta t$. For example, (1,1,2,2) gives a time-step of 1.0 fs, and (2,2,2,2) gives a time-step of 4.0 fs. For a similar accuracy level, the r-RESPA/TFMM method is able to use a time-step nearly 8–9 times larger than that of velocity Verlet. For velocity Verlet, $E_{total}$ starts drifting to higher energies with time when the time-step exceeds 1.0 fs, whereas r-RESPA/TFMM is quite stable even for an overall time-step as large as 4.0 fs.

Figure 3B:
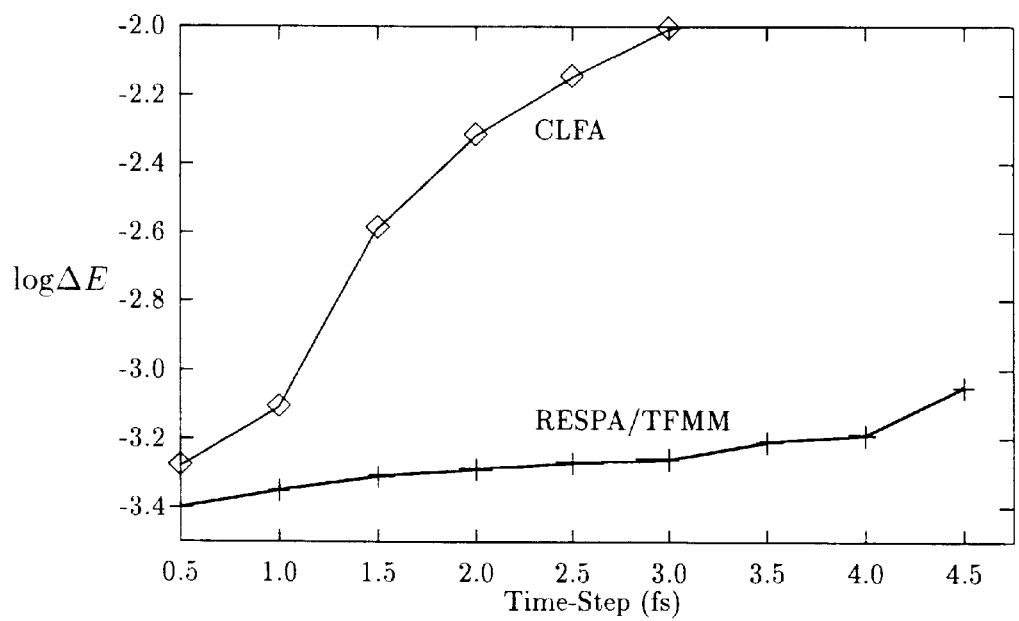

A comparison of r-RESPA/TFMM with CLFA is made. This method, denoted the Constant Long-range Force Approximation (CLFA), is a frequently used approximation whereby the long range forces are treated as effectively constant over a number of time-steps n, with a standard integrator such as velocity Verlet. In order to make the comparison, the identical "short/long" range force breakup for nonbonded forces in two methods are employed. That is, the near zone is chosen as "short" range ($r \leq 8.0$ Å for vdW, and nearest-neighbor boxes for electrostatic force), and medium and far zones as "long" range. In both regions there are contributions from vdW and electrostatic forces. The overall time-step for CLFA is n$\delta$t. The energy conservation parameter log($\Delta$E) is plotted as a function of overall time-step in FIG. 3B for both CLFA and r-RESPA/TFMM. The constant long range approximation leads to very poor energy conservations in this case, whereas r-RESPA/TFMM remains quite stable for significantly larger time-steps.

Furthermore, r-RESPA/TFMM was even faster than CLFA for time-steps larger than 2.0 fs. Log($\Delta$E) will decrease to some extent for CLFA if a small time-step of $\delta t$=0.25 fs is used in CLFA, or is used both near and medium zones are used as "short"-range, but log($\Delta$E) still increases much faster with the overall time-step than r-RESPA/TFMM, i.e., it was not as stable as r-RESPA/TFMM. The CPU time required in CLFA increases at the same time, which is not desired.

Table 3 summarizes some results from the three different methods: velocity Verlet, CLFA, and r-RESPA/TFMM for comparison.

Spectral Density Comparison

To explore the question of whether r-RESPA/TFMM does indeed generate the correct dynamics for the system, a spectral density $I(\tilde{v})$ as a function of the frequency $\tilde{v}$ in wave numbers obtained from the two methods was compared, velocity Verlet and r-RESPA/TFMM, where $$I(\tilde{v}) = \int_0^\infty C_V(t)\cos(2\pi c\tilde{v}t)dt \qquad \text{(Equation No. 42)}$$

and $C_v(t)$ is the normalized velocity autocorrelation function of the system, $$C_V(t) = \frac{\left\langle \sum_{i=1}^{N} v_i(t)\cdot v_i(0) \right\rangle}{\left\langle \sum_{i=1}^{N} v_i(0)\cdot v_i(0) \right\rangle}, \qquad \text{(Equation No. 43)}$$

where <...> signifies ensemble average.

The speed of light is c, $v_i(t)=(v_x(t), v_y(t), v_z(t))$ is the velocity of atom i at time t, and N is the total number of atoms. The protein interleukin 8 (3il8) for the spectrum simulation was used as a test case. The velocity autocorrelation function and its infrared spectrum were obtained from 5 ps MD runs for three different cases:

(1) velocity Verlet with time-step 0.25 fs (Verlet_0.25 fs)
(2) velocity Verlet with time-step 0.50 fs (Verlet_0.5 fs)
(3) r-RESPA/TFMM with time-step 4.0 fs, (2,2,2,2) combination (RESPA/TFMM_4.0 fs)

Figure 4A:
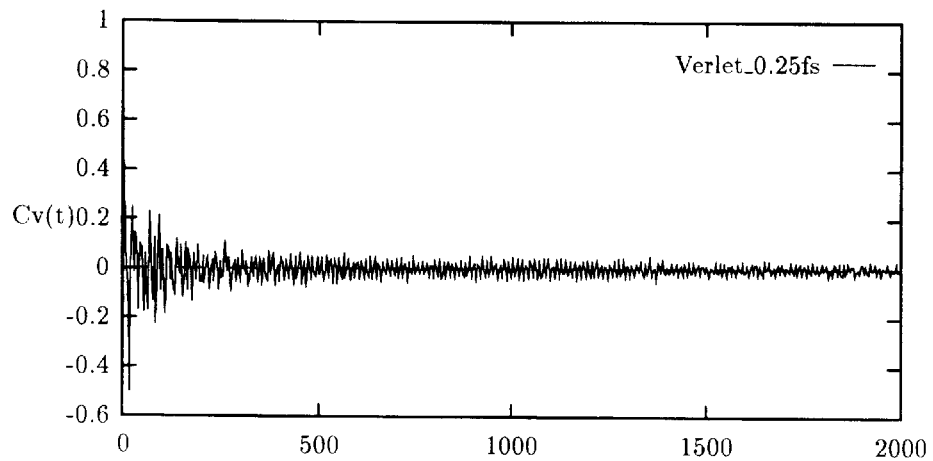
FIGS. 4A–4C: The velocity autocorrelation function $C_v(t)$ as a function of time for three cases.
Figure 4B:
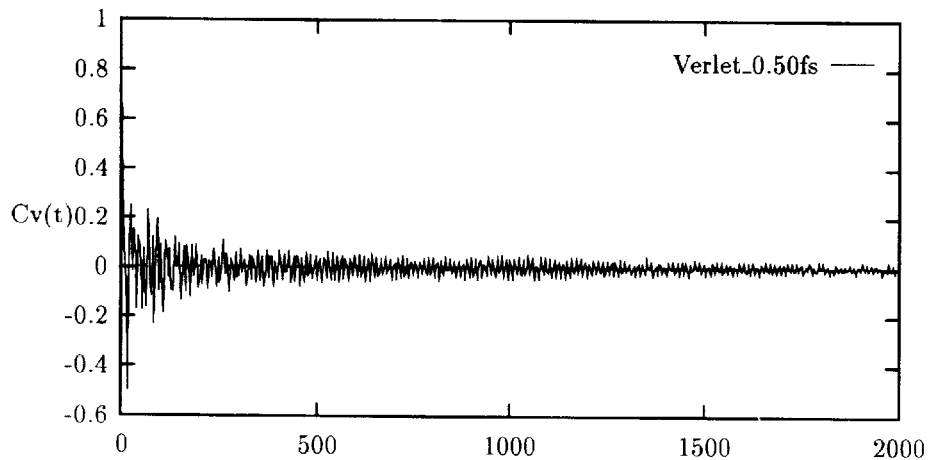
Figure 4C:
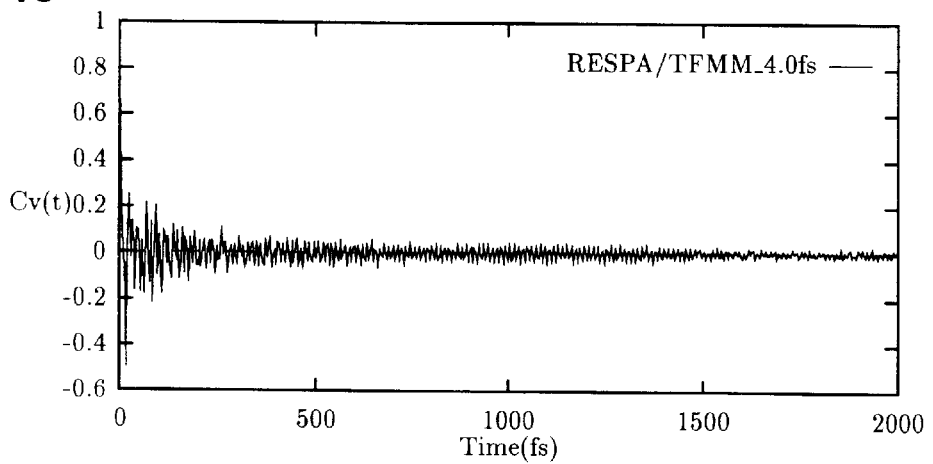
Figure 5:
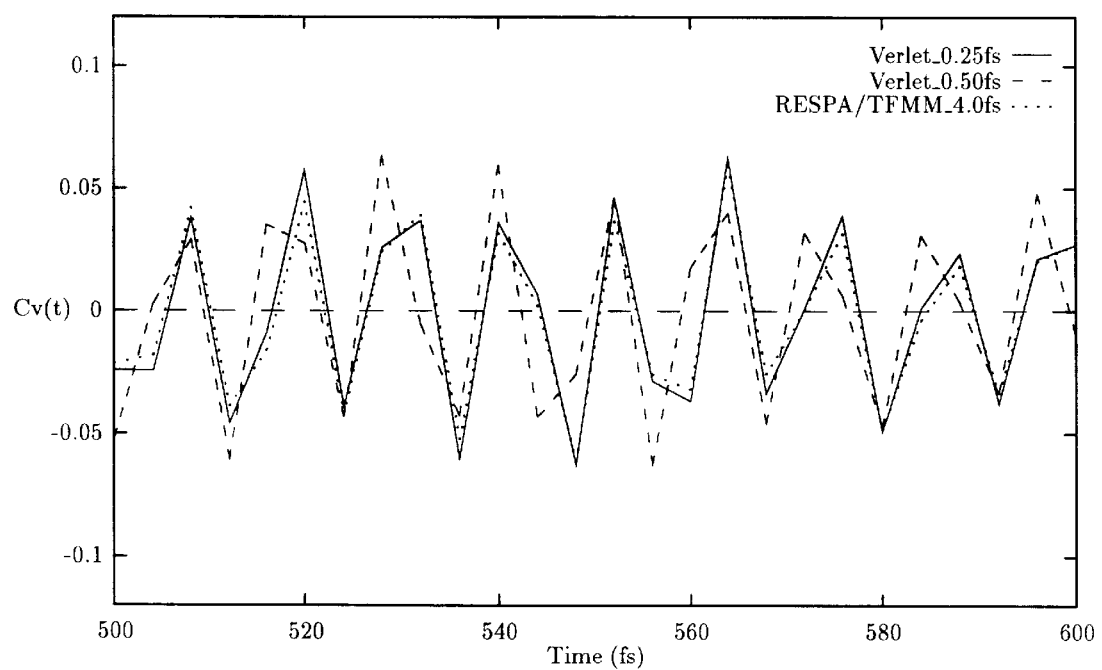
FIG. 5: Comparison of the velocity autocorrelation functions in details: velocity Verlet with $\Delta t=0.25$ fs (solid line), velocity Verlet with $\Delta t=0.50$ fs (dash line), and r-RESPA/TFMM with overall time-step 4.0 fs (combination of (2,2,2,2) with $\delta t=0.25$ fs, dotted line).
Figure 6A:
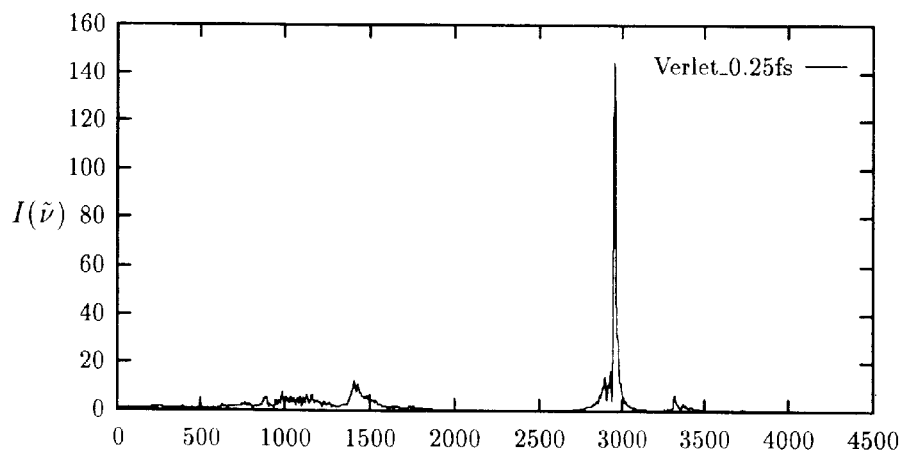
FIGS. 6A–6C: Spectral intensity $I(\tilde{v})$ as a function of wavenumber for three cases.
Figure 6B:
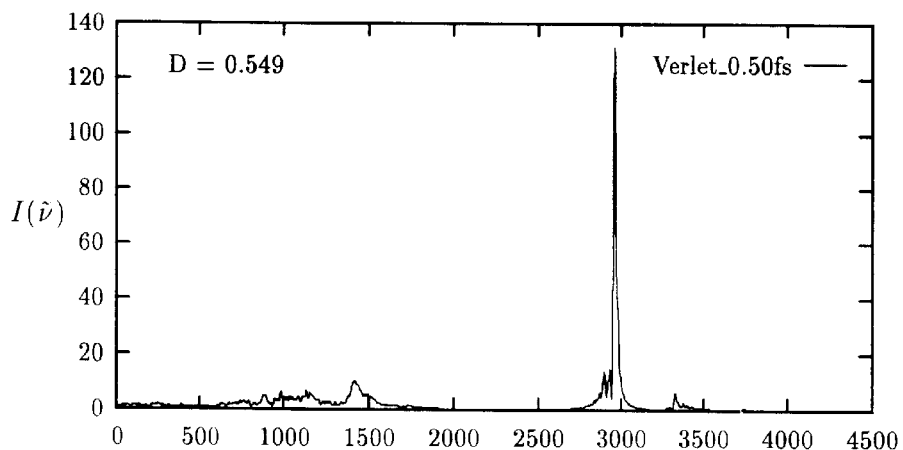
Figure 6C:
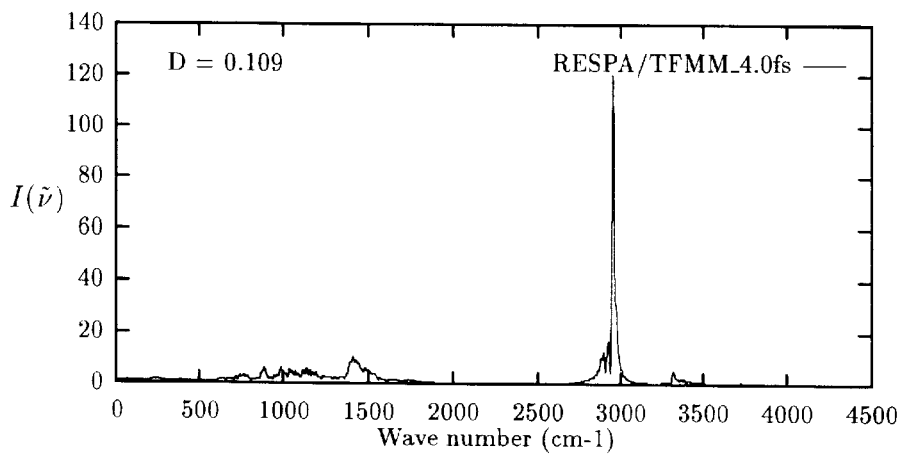
Figure 7A:
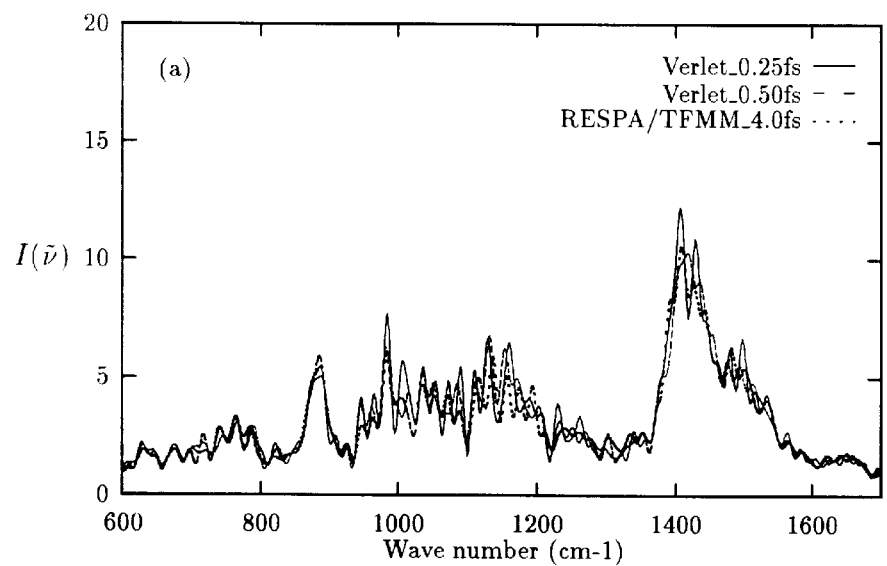
FIGS. 7A–7D: Comparison of the details of the spectral intensities $I(\tilde{v})$ in FIGS. 6A–6C in four frequency regions, velocity Verlet with $\Delta t=0.25$ fs (solid line), velocity Verlet with $\Delta t=0.50$ fs (dash line), and r-RESPA/TFMM with overall time-step 4.0 fs (combination of (2,2,2,2) with $\delta t=0.25$ fs, dotted line). Intensities are in arbitrary units.
Figure 7B:
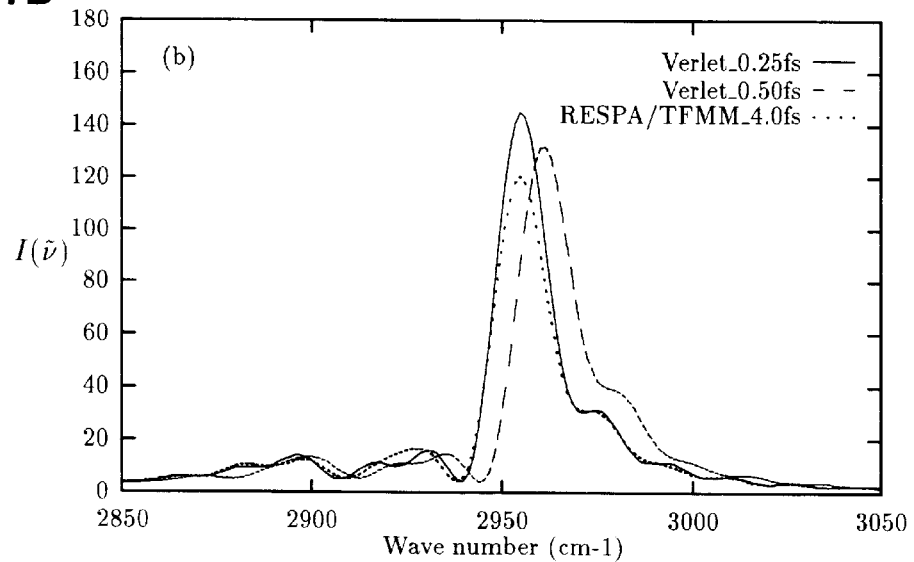
Figure 7C:
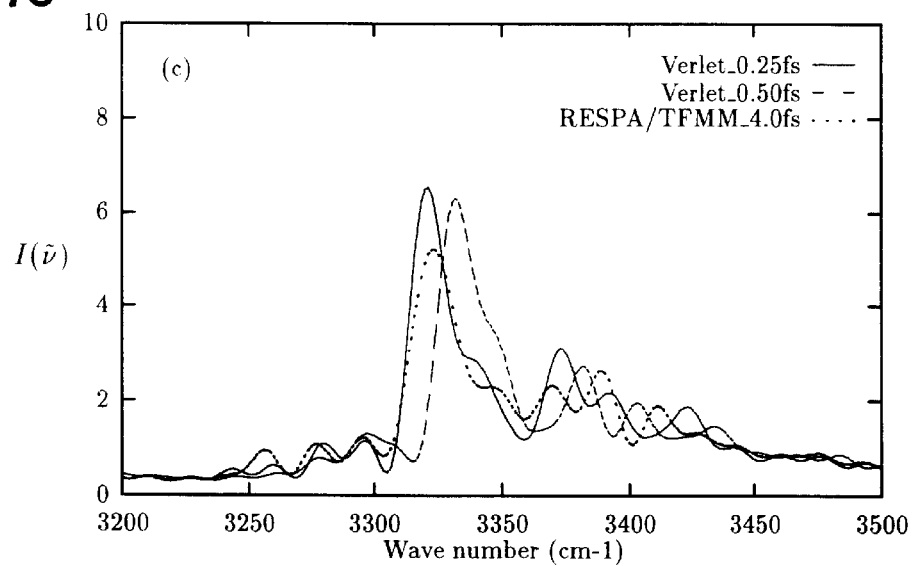
Figure 7D:
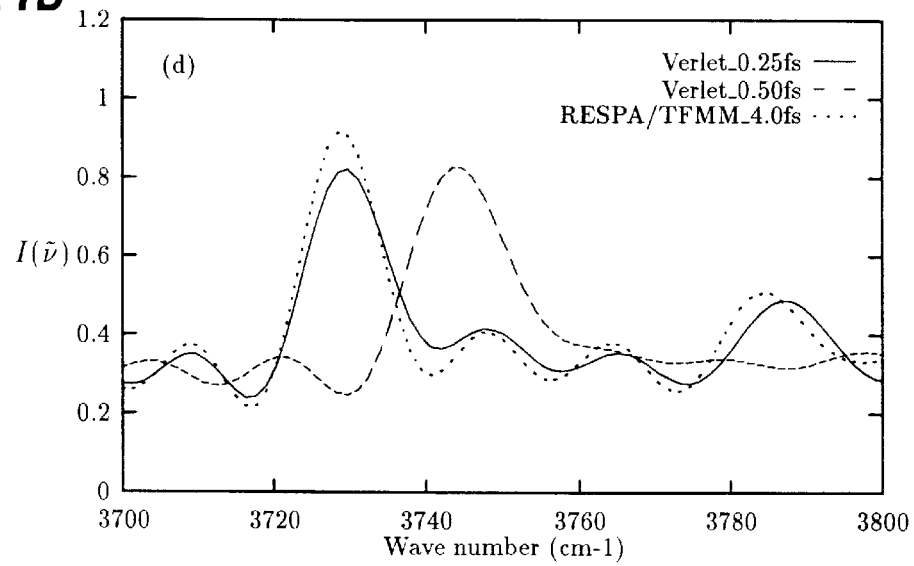

The Verlet_0.25 fs case represents the "exact" result. FIGS. 4A–4C show the autocorrelation functions for the three cases (only 2 ps is plotted). The three cases look similar, but the details shown in FIG. 5 indicate that the autocorrelation function of Verlet_0.50 fs actually differs from the Verlet_0.25 fs after 0.5 ps. However, RESPA/TFMM_4.0 fs stays very close to Verlet_0.25 fs for 1.2 ps. These differences in autocorrelation functions result in the differences between the three corresponding spectral profiles given in FIGS. 6A–6C. The sharp peak at 2955–2985 cm$^{-1}$ is due to the C—H stretch vibrations, and the small peak near 3320 cm$^{-1}$ is due to the hydrogen-bonded O—H stretches, while the small shoulders around 600–1200 cm$^{-1}$ and small peaks around 1500 cm$^{-1}$ belong to various bending modes, as well as C—C and C=O stretch vibrations.

In order to establish a quantitative estimate of the accuracy of the resulting spectral densities, one may consider [24, 34]

$$D \equiv \arccos\left(\frac{\vec{S}_1 \cdot \vec{S}_2}{|\vec{S}_1||\vec{S}_2|}\right), \qquad \text{(Equation No. 44)}$$

where $$\vec{S} = (s_1, \ldots, s_n), \qquad \text{(Equation No. 45)}$$

and the $s_i$ are the spectral components at frequency i. The quantity D in the above equation can be viewed as the angle between the vectors $S_1$ and $S_2$. If the two spectra are identical, then D=0, whereas, if they are uncorrelated, D=Π/2. The "exact" spectral density to be defined as that obtained from a MD simulation using the velocity Verlet integrator with a time-step of 0.25 fs was taken as a reference. The value of D was then calculated with respect to this reference spectral density for the other two cases. The following results were obtained: D=0.549 for that of velocity Verlet using a time-step of 0.5 fs, and D=0.109, for r-RESPA/TFMM with an overall time-step 4.0 fs. Thus, r-RESPA/TFMM not only reduces the CPU time, but also shows better spectra compared to the velocity Verlet integrator using a time-step of 0.5 fs.

The poor D value for the velocity Verlet with Δt=0.5 fs can be attributed to a numerically induced "blue shift" evident at the higher frequencies of the spectral density [24, 19]. To illustrate this, FIGS. 7A–7D show the detailed spectra for the three cases in four different frequency regions. The differences between the 3 cases are small in the frequency region 600–1600 cm$^{-1}$, but the Verlet_0.50 fs spectrum starts to differ from Verlet_0.25 fs at higher frequencies. The sharp C—H stretch peak at 2954 cm$^{-1}$ shifts to 2961 cm$^{-1}$, the hydrogen-bonded O—H stretch shifts from 3321 cm$^{-1}$ to 3332 cm$^{-1}$, and the free O—H stretch shifts from 3728 cm$^{-1}$ to 3745 cm$^{-1}$. The RESPA/TFMM_4.0 fs spectrum agrees with Verlet_0.25 fs very well, and no evident shifts are found for these peaks. This indicates that the smallest time-step for stretching is critical in generating the correct infrared spectra. Also, the fact that Verlet_0.50 fs agrees well with Verlet_0.25 fs at low frequencies, but differs at higher frequencies (the higher the frequency, the larger the blue shift) indicates that for high frequency vibrations, such as C—H, O—H stretch, a time-step of less than 0.50 fs is necessary.

CPU Timing Comparison

In the FMM model the space is generally subdivided into cubic boxes [11, 25, 26, 32, 35]. This subdivision of space makes it simpler to construct the FMM method and easier to determine the error bounds). The use of rectangular boxes instead of cubic boxes will further reduce the number of vacant boxes, and will also reduce the set of pair numbers in the near region which must be evaluated directly. Although using rectangular boxes may lower the accuracy for systems with very high aspect ratios, for most proteins the accuracies are perfectly acceptable.

Figure 8:
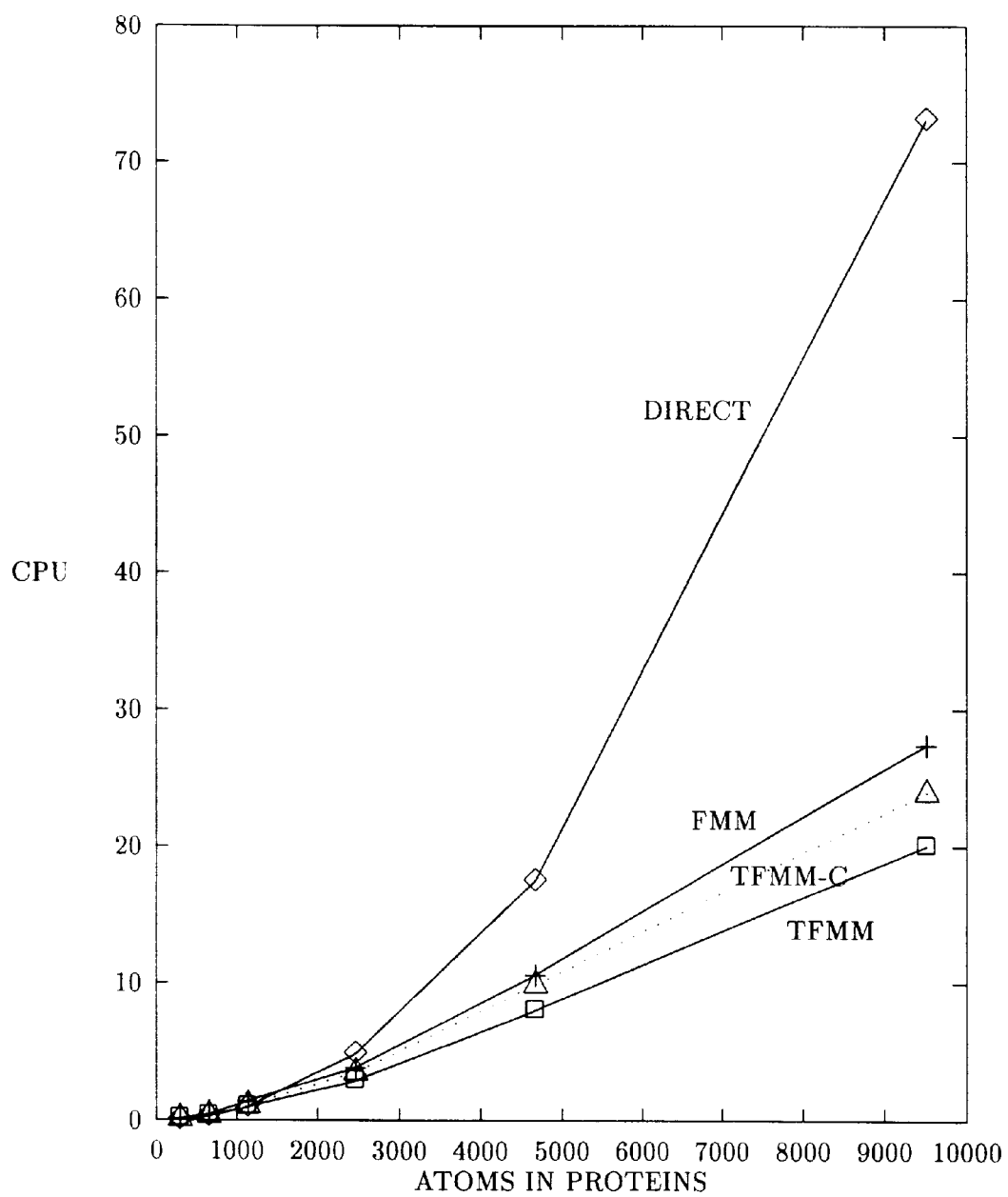
FIG. 8: Comparison of the performances of the conventional FMM (cubic box), top-down FMM with cubic-box subdivision (TFMM-C), and top-down FMM with rectangular-box subdivision (TFMM) in calculating the long range electrostatic interactions for proteins. Parameters p=4 and ws=2 are used in fast multipole method, and parameter n (total levels in the box tree) is listed in Table 1. CPU times for direct evaluation of the Coulomb interactions are also included for comparison. The CPU time (in seconds) is for RISC6000/MODEL 590 computers.

FIG. 8 shows the CPU times for the calculation of the electrostatic potential and the forces in one MD time-step for FMM (cubic box), the top-down FMM with cubic box (TFMM-C) and the top-down FMM with rectangular boxes (TFMM). The optimum parameters (n, p, ws) obtained herein were used. The top-down FMM with cubic boxes was found to be up to 15% faster than the conventional FMM depending on the inhomogeneity of the proteins. The percentages of the vacant boxes for these proteins are from 14% (lcrn) to 37% (lprc) when using cubic boxes, and this percentage may be a normal range for most proteins. However, the percentage of the vacant boxes depends on the tree levels used; the higher the tree level, the larger the percentage. Here, the optimum tree levels listed in Table 1 were used; that is, the average atom number in the smallest box is roughly 2–10. The TFMM, using both top-down recursion and rectangular boxes, however, was found to be 20–40% faster than the normal FMM, indicating that it may be useful for noncubic inhomogeneous systems, such as proteins.

Figure 9:
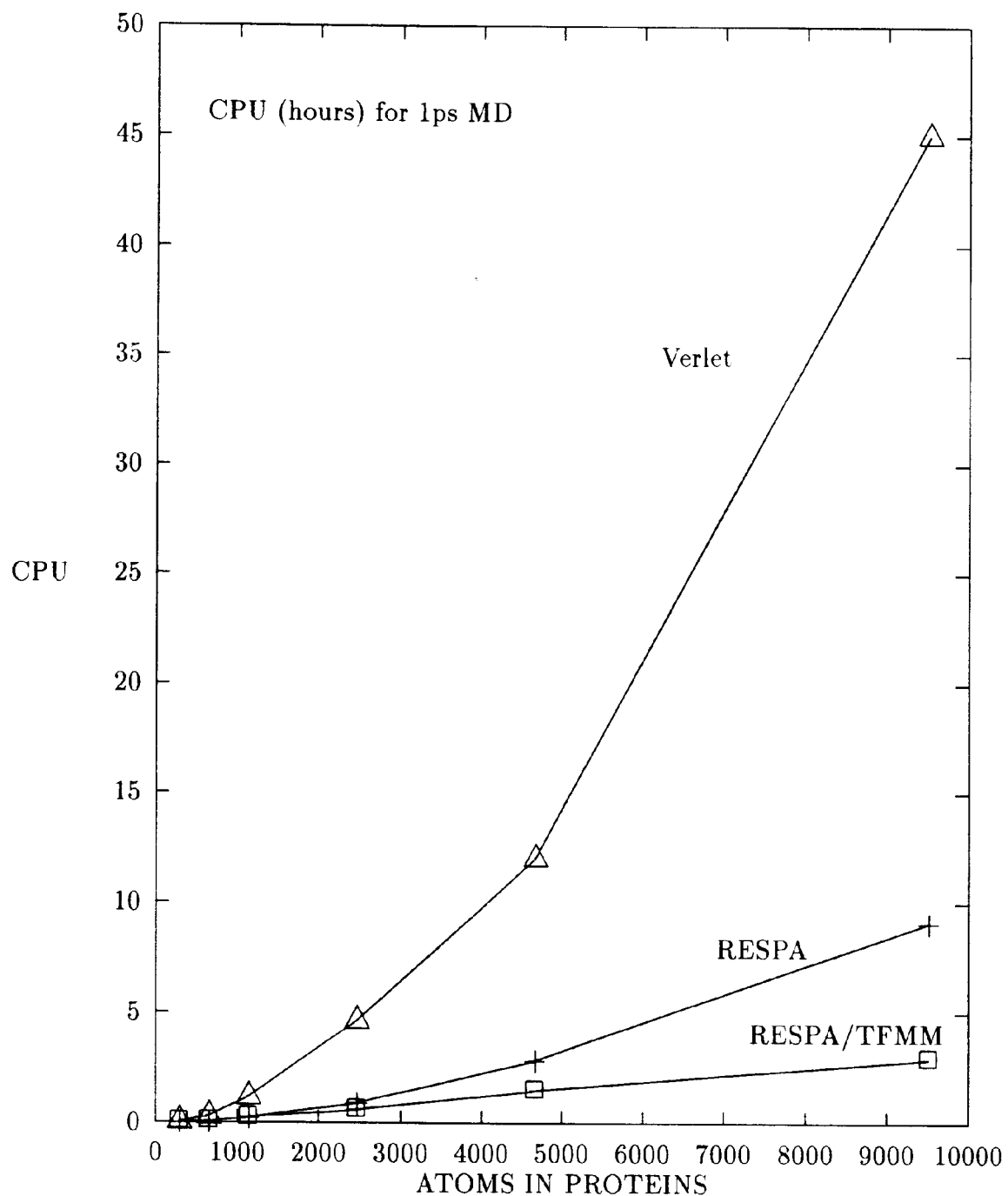
FIG. 9: CPU times (in hours) for 1 ps MD runs for various proteins using 3 different methods, direct velocity Verlet with a time-step 0.5 fs, r-RESPA with direct evaluation of electrostatic forces and an overall time-step of 4.0 fs, and r-RESPA/TFMM with an overall time-step 4.0 fs (combination of (2,2,2,2) in force breakup). The energy conservation parameter log $\Delta E$ for the three methods are comparable. The CPU time (hours) is for RISC6000/MODEL 590 computers.

The CPU saving of r-RESPA versus velocity Verlet results from the fact that in r-RESPA, a time-step ~8 times larger than that of velocity Verlet for the far region nonbonded forces may be used (which are usually the most CPU consuming interactions). FIG. 9 shows plots of the total CPU times for 1 ps MD runs using velocity Verlet with a time-step 0.5 fs and r-RESPA with an overall time-step 4.0 fs (combination of (2,2,2,2) in force separation). r-RESPA is about 4–6 times faster than velocity Verlet for various proteins with the same level of accuracy.

Implementation of the TFMM for electrostatic interactions in r-RESPA will further reduce the CPU time for Coulomb interactions compared to the direct evaluation. The total CPU times for r-RESPA/TFMM are also shown in FIG. 9 for comparison. It was determined that for a protein larger than ~1000 atoms the TFMM is faster than the direct evaluation, indicating that the crossover point is about 1000 atoms. For the protein lprc, the TFMM further reduces the total CPU time by a factor of 3, i.e., the r-RESPA/TFMM is ~3 times faster than r-RESPA for a protein with 9513 atoms (in fact, the CPU time saving for electrostatic forces is about 4–5, the factor 3 is for total CPU time saving). This CPU time saving resulted from the elegant use of the multipoles and local field expansions in FMM as well as the top-down recursion and non-cubic box separation.

Replotting the CPU time in FIG. 9 on a log scale, $\log(T_{CPU})$ vs $\log(N)$, and fitting it with a straight line, $$\log(T_{CPU})=c_0+c_1\log(N), \qquad \text{(Equation No. 46)}$$

then the CPU time scales with N as:

Velocity Verlet: $T_{CPU} \sim N^{1.90}$ r-RESPA: $T_{CPU} \sim N^{1.79}$ r-RESPA/TFMM: $T_{CPU} \sim N^{1.32}$ The CPU time scales nearly as $N^2$ in the velocity Verlet integration method. The r-RESPA method reduces CPU time by a factor of 4–6 for various proteins, and reduces the order from 1.90 to 1.79. After applying TFMM in r-RESPA, the CPU time scales almost linearly with the number of atoms, which is also clear in FIG. 9. Thus, an even larger speedup for larger biosystems is expected. Also, it is no longer necessary to set up pairlists for these long-range pairwise Coulombic interactions, so the memory requirement is also of order of $O(N)$ rather than $O(N^2)$.

To gain a deeper insight into the CPU timings and savings for different forces using different methods, detailed CPU timings are listed in Table 4 for the largest protein simulated, the photosynthetic reaction center. In order to reduce computational effort, this data was collected over only 0.1 ps MD runs. 99% of CPU time is spent on the calculation of the nonbonded forces (vdW and Coloumb forces) when standard methods are used, which indicates that more efficient methods for computing nonbonded forces are highly desirable. The r-RESPA and FMM are designed for this purpose. Compared to the velocity Verlet with time-step 0.5 fs, the r-RESPA, with a time-step 4.0 fs (combination (2,2,2,2)) and a comparable level of accuracy, lowers the total CPU time from 15566 s to 3489 s, by a factor of 4.46. The r-RESPA/TFMM further reduces the total CPU time from 3489 s to 1154 s, by a factor of 3.02, and reduces the CPU time for the calculation of electrostatic forces from 2993 s to 680 s, by a factor of 4.40. Overall, the r-RESPA/TFMM method lowers the total CPU time by a factor of 15 and lowers the CPU time for electrostatic forces by a factor of 20. Since this is for the high accuracy $\log(\Delta E)<-3.0$ constant-energy MD simulations, the CPU time saving is significant. If some loss of accuracy can be tolerated, such as in constant-temperature MD simulations where velocities are rescaled artificially, an even larger speedup may be obtained by using p=3

(octapole) or p=2 (quadrupole). In addition, the best combination of the force separation in r-RESPA is found to be (2,2,2,2) rather than (1,1,1,16), which could be physically reasonable, since the intrinsic separation in time scales for the different forces increases gradually.

It is necessary to use very small time-steps, such as 0.25 fs, to obtain the reasonable spectral densities for vibrational stretches, such as CH, O—H stretching. So, compared to the velocity Verlet with a time-step 0.25 fs and direct evaluation of Coulomb forces, a CPU time speed up of ~30 would be expected for r-RESPA/TFMM for a protein with 9513 atoms. Since 0.5 fs is generally used for MD simulations of proteins, a comparison is made to velocity Verlet with time-step 0.5 fs. Larger time-steps, such as 0.8 fs, and 1.0 fs, are also reported for MD simulations of proteins by using SHAKE [36, 37]. However, these simulations using SHAKE will affect spectral densities. For example, there will be no C—H peak in spectra if C—H bond length is constrained. Furthermore, SHAKE will affect some other properties, such as time dependent quantities [14, 15] and spectral densities associated with the main chain and side chain torsional motion [37].

The new MD method developed uses a new version of the Fast Multipole Method (FMM) and the reversible Reference System Propagator Approach (r-RESPA), and is a significant improvement over other approachs in dealing with the two main bottlenecks in simulating biosystems:

(a) calculating the full long-range Coulombic interactions; and (b) treating the intrinsic differences in timescales for various interactions.

A new version of the Fast Multipole Method (FMM) with top-down recursive generation of the multipoles and rectangular box subdivisions is proposed, which is 20–40% faster than the standard FMM method for simulations of proteins in vacuo. By using the new version of FMM, the requirement for CPU time and memory scales as O(N) instead of O(N$^2$), and the total CPU time is reduced by a factor of ~3 for a protein with 9513 atoms at an efficient accuracy level.

The r-RESPA method uses a time-step 8–9 times larger than that of the standard velocity Verlet method (with time-step 0.5 fs) with even better infrared spectra for biomolecules, which results in a speed up of 4–6 times in total CPU time. The r-RESPA generates a more stable MD simulation than the frequently used constant long-range force approximation.

By using both the modified FMM and r-RESPA, the computational task is now nearly O(N), which makes possible efficient MD simulations of very large biomolecular systems.

For the photosynthetic reaction center (9513 atoms) the new MD method leads to a 20-fold CPU time speedup for electrostatic interactions, and a 15-fold speedup of the total MD simulation compared to standard methods at the same level of energy conservation, with even better spectra properties.

The method described herein should be very useful for simulations of large proteins surrounded by water molecules, and such applications are under way.

Extension of FMM to Periodic Systems

In order to simulate proteins in water, a realistic representation needs both explicit solute and solvent molecules with periodic boundary conditions. This can be achieved efficiently by extending the FMM to periodic systems. The first implementation of the FMM for systems with periodic boundary conditions is that of Schmidt and Lee [38], although Greengard's dissertation [39] contains a brief description of the main ideas. However, reduction of the Schmidt and Lee formula to the Ewald limit could not be made. This section enlarges on the method of Schmidt and Lee and presents the derivation of formulas which reduce to regular Ewald in the proper limits.

In the description below it is assumed that the simulation box is cubic and its linear dimension is b. To introduce periodic boundary conditions it is convenient to think of the simulation system as consisting of an infinite lattice of exact replicas of the unit cell. One can focus on one particular cell among them and call it the "central" box; the others will be called the "proper copies." The potential produced by all the proper copies at a point x inside the central box can be calculated in a way similar to that discussed in the above section. Schmidt and Lee regarded these proper copies as "virtual" clusters and applied the same FMM algorithm to them as to the central box. More precisely, the proper copies can be subdivided into first and second neighbors of the central box and all the others. The third neighbors and more distant copies, that is, those for which at least one component of n is larger than 2, will be called "distant copies." The local field coefficients from these "distant copies" at the central box can then be expressed by $$\sum_n L_{lm}(Q; A - bn) = \sum_{j=0}^{\infty} \sum_{k=-l}^{l} \sum_n T_{lm,jk}^{LM}(bn) M_{jk}(Q; A) \qquad \text{(Equation No. 47)}$$

In the summation of transform operator $T_{lm,jk}^{LM}(bn)$, which transforms multiples of "distant copies" to local field of the central box, an infinite sum similar to the Ewald sum must be evaluated, $$S_l^m \equiv \sum_{n \neq 0} \frac{Y_l^m(\hat{n})}{\|n\|^{l+1}}. \qquad \text{(Equation No. 48)}$$

The sum is conditionally convergent for $1 \leq l \leq 2$ and absolutely convergent for $l > 2$. The computation is carried out using an extension of the Ewald summation method, which is parallel to that given by de Leeuw et al. [41]. To obtain a convergent sum that can be manipulated, replace Equation No. 48 by $$S_l^m = \lim_{s \to 0^+} \sum_{n \neq 0} \frac{\|n\|^l Y_l^m(\hat{n})}{\|n\|^{2l+1}} e^{-s\|n\|^2}. \qquad \text{(Equation No. 49)}$$

With this regularization the sum for odd l vanishes identically because of reflection symmetry. After some algebra, the sum over all proper copies can be shown:

$$S_l^m = \sum_{n \neq 0} \frac{Y_l^m(\hat{n})}{\|n\|^{l+1}} \qquad \text{(Equation No. 50)}$$

$$= \sum_{n \neq 0} Y_l^m \frac{(\hat{n})}{\|n\|^{l+1}} I_{l+\frac{1}{2}}(\alpha^2 \|n\|^2) +$$

$$\sum_{n \neq 0} \pi^{l-\frac{1}{2}} i^l Y_l^m(\hat{k}) \|k\|^{l-2} e^{-\frac{\pi^2 \|k\|^2}{\alpha^2}}$$

where the function $l_r(x)$ is defined as $$I_r(x) = \int_x^\infty t^{r-1} e^{-t} dt.$$ (Equation No. 51)

It can be shown that the above function satisfies the recurrence relation $$I_{\frac{1}{2}}(x) = \sqrt{\pi}\left(1 - erf(\sqrt{x})\right)$$ (Equation No. 52)

$$I_r(x) = x^{r-1} e^{-x} + (r-1) I_{r-1}(x),$$ (Equation No. 53)

which is valid for any r, (r=l+½). The function erfc(x) is the usual complementary error function.

Thus, the local field of all multiples of "distant copies" can be transformed into the central box, which is then used to calculate the electric potential and forces. The results embodied in Equation No. 50 resembles the Ewald summation formula [41,42] but differs from the latter in a key aspect: whereas the Ewald summation formula gives the Wigner potential at each point in the unit cell, Equation No. 50 gives just the nontrivial part of the coefficients of the translation matrix that converts the unit cell's multipole moments into a local expansion around its center of the potential produced by all the proper copies.

Proteins in Water

The effect of solvating a protein was studied on three systems: ribonuclease H (2rn2), arabinose-binding protein (8abp), and lysozyme. In all cases the protein is put in the center of a pre-equilibrated SPC water bath, which is chosen large enough to hold the protein. For the lysozyme case a very large water box, 76 Å on each side, was used. The water molecules that overlap with the protein are deleted in all cases. After these steps the number of remaining water molecules are: (a) 1,982 for ribonuclease H; (b) 5,990 for arabinose-binding protein; and (c) 14,093 for lysozyme. The solvated proteins are then minimized by using steepest descent method, and equilibrated to about 300K by velocity resealing. After full equilibration of the protein-water system has been achieved, which can take weeks of central processing unit (CPU) time for large protein systems, a constant energy simulation can be run.

The results described below were obtained from 1 picosecond (ps) molecular dynamics (MD) simulations of 2rn2/water (8,412 atoms), 8abp/water (22,913 atoms), and lysozyme/water (44,259 atoms). Two algorithms for calculating electrostatic forces with periodic boundary conditions, Ewald sum and periodic FMM; and two integrators, Verlet and r-RESPA, are compared.

For the Ewald method, a cutoff $r_c$=15.0 Å~18.0 Å and η=8~12 are used in the real space, and $k_{max}$=10~15 is used in the reciprocal space for the three different systems to achieve optimal parameters in the Ewald method. For the periodic FMM method, p=7 is used to achieve high accuracy for water molecules (it is found that for water molecules a higher p value should be used since atomic cutoffs are being utilized). The tree levels of L=3, L=4, L=4 are used for 2rn2/water, 8abp/water, and lysozyme/water respectively. The r-RESPA force separations are similar to the protein systems in vacuo (protein/vacuum systems) discussed in above sections, except that all the bonding forces are included in one stage in protein-water systems because bond length constraints are being used, while they are separated into two stages in protein-vacuum systems. To be parallel to the above protein/vacuum results, one uses $n_2$, $n_3$, $n_4$ in separations instead of $n_1$, $n_2$, $n_3$, because the first two stages in protein/vacuum are now combined into one stage.

Table 5 lists log(ΔE) and CPU times for protein 2rn2/water, 8abp/water, and lysozyme/water for different methods. It is apparent that the combined r-RESPA/FMM algorithm (denoted as R-FMM in Table 5) is much faster than the standard Verlet/Ewald method (denoted as V-Ewald in Table 5) for large solvated protein systems with periodic boundary conditions. The CPU times for the Verlet/Ewald method are found to be 27.7, 187.9, and 562 ksec/ps for the 2rn2/water, 8abp/water and lysozyme/water systems, respectively, with an accuracy level of log(ΔE) ~-3.20. In contrast, the CPU times for the r-RESPA/FMM method are only 8.48, 16.4, and 24.1 ksec/ps, respectively, with the same or better accuracy level. This gives a factor of 3.3, 11.4, and 23.3 in CPU time savings for systems with about 8,000, 22,000, and 44,000 atoms at the same accuracy level. The CPU time savings will be even more promising for even larger systems, such as solvated nucleic acid systems. Thus, it is observed that r-RESPA/FMM provides a computational advantage over standard Verlet/Ewald even for the smallest macromolecular system simulated, of about 8,000 atoms.

References

[1] J. A. McCammon and S.C. Harvey. *Dynamics of Proteins and Nucleic Acids*. Cambridge University Press, Cambridge, 1987.

[2] K. M. Merz Jr. and S. M. Le Grand. The protein folding problem and tertiary structure prediction. Birkhäuser, Boston, 1994.

[3] B. R. Brooks, R. E. Bruccoeri, B. D. Olafson, D. J. States, S. Swaminathan and M. Karplus. *J. Comp. Chem.*, 4:187, 1983.

[4] A. Windemuth and K. Schulten. *Mol. Simul.*, 6:121, 1991.

[5] L. Verlet. *Phys. Rev.*, 159:98, 1967.

[6] W. C. Swope, H. C. Anderson, P. H. Berens, and K. R. Wilson. *J. Chem. Phys.*, 76:637, 1982.

[7] R. W. Hockney and J. W. Eastwood. *Comutational Simulation Using Particles*. McGraw-Hill, New York, 1981.

[8] R. W. Hockney. *Methods Comput. Phys.*, 9:136, 1970.

[9] A. Appel. *SIAM J. Sci. Stat. Comp.*, 6:85, 1985.

[10] J. E. Barnes, and P. Hut. *Nature*, 324:446, 1986.

[11] L. Greengard, and V. Rokhlin. *J. Comp. Phys.*, 60:187, 1985.

[12] J. P. Ryckaert, G. Ciccotti, and H. J. C. Berendsen. *J. Comp. Phys.*, 23:327, 1977.

[13] H. C. Anderson. *J. Comp. Phys.*, 52:24, 1983.

[14] W. F. van Gunsteren and M. Karplus. *Macromolecules*, 15:1528, 1982.

[15] S. Toxaerd. *J. Chem. Phys.*, 87:6140, 1987.

[16] M. P. Allen and D. J. Tildesley. *Computer Simulation of Liquids*. Oxford University Press, Oxford, 1987.

[17] O. Teleman, and B. Jönsson. *J. Comp. Chem.*, 7:58, 1986.

[18] M. E. Tuckerman, and B. J. Berne. *J. Chem. Phys.*, 95:8362, 1991.

[19] D. D. Humphreys, R. A. Friesner, and B. J. Berne. *J. Phys. Chem.*, 98:6885, 1994.

[20] R. D. Swindoll, and J. M. Haile. *J. Comp. Phys.*, 53:289, 1984.

[21] M. E. Tuckerman, B. J. Berne, and G. J. Martyna. *J. Chem. Phys.*, 97:1990, 1992.

[22] H. F. Trotter. *Proc. Am. Math Soc.*, 10:545, 1959.

[23] M. Watanabe, and M. Karplus. *J. Chem. Phys.*, 99:8063, 1993.

[24] P. Procacci, and B. J. Berne. *J. Chem. Phys.*, 101:2421, 1994.

[25] C. A. White and M. Head-Gorden. *J. Chem. Phys.*, 101:6593, 1994.

[26] Hong-Qiang Ding, N. Karasawa, and W. A. Goddard III. *J. Chem. Phys.*, 97:4309, 1992.

[27] M. E. Tuckerman, G. J. Martyna, and B. J. Berne. *J. Chem. Phys.*, 94:6811, 1991.

[28] M. E. Tuckerman, and B. J. Berne. *J. Chem. Phys.*, 98:7301, 1993.

[29] F. Mohamadi, N. G. J. Richards, W. C. Guida, R. Liskamp, M. Lipton, C. Caufield, G. Chang, T. Hendrickson, and W. C. Still. *J. Comp. Chem.*, 11:440, 1990.

[30] S. J. Weiner, P. A. Kollman, D. T. NGuyen, and D. A. Case. *J. Comp. Chem.*, 7:230, 1986.

[31] W. L. Jorgensen and J. Tirado-Rives. *J. Am. Chem. Soc.*, 110:1657, 1988.

[32] J. A. Board Jr., J. W. Causey, J. F. Leathrum Jr., A. Windermuth and K. Schulten. *Chem. Phys. Lett.*, 189:89, 1992.

[33] W. F. van Gunsteren and H. J. C. Berendsen. *Mol. Phys.*, 34:1311, 1977.

[34] J. Skilling, and R. K. Bryan. *Mon. Not. R. Astro. Soc.*, 211:111, 1984.

[35] J. Shimada, H. Kaneko, and T. Takada. *J. Comp. Chem.*, 15:28, 1994.

[36] M. Marchi, J. N. Gehlen, D. Chandler, and M. Newton. *J. Am. Chem. Soc.*, 115:4178, 1993.

[37] M. Watanabe, and M. Karplus. *J. Phys. Chem.*, 99:5680, 1995.

[38] K. E. Schmidt and M. A. Lee, *J. Stat. Phys.* 63:1223, 1991.

[39] L. Greengard, *The Rapid Evaluation of Potential Fields in Particle Systems* (MIT Press, Cambridge, Mass., 1988).

[40] K. Esselink, *Comp. Phys. Comm.* 87:375, 1995.

[41] S. W. de Leeuw, J. W. Perram, and E. R. Smith, *Proc. R. Soc. Lond.*, A:27, 1980.

[42] M. P. Allen and D. J. Tildesley, *Computer Simulation of Liquids,* Oxford Science Publications (Oxford University Press, Oxford, 1991).

TABLE 1

Tree level n and the average particle numbers in the finnest-level box $N_o$ used in FMM for various proteins with total atom number N.

| Protein | 4insb | 1crn | 3il8 | 2rn2 | 8abp | 1prc |
|---|---|---|---|---|---|---|
| N | 292 | 655 | 1144 | 2470 | 4674 | 9513 |
| n | 2 | 2 | 3 | 3 | 3 | 4 |
| $N_o$ | 4.56 | 10.23 | 2.24 | 4.82 | 9.13 | 2.32 |

TABLE 2

Accuracy and speed up of the new version of the Fast Multipole Method for various proteins in both ws = 1 and ws = 2 cases. The CPU time of the direct method is also included for comparison. For each column, the three numbers are CPU time, $\Delta\Phi$ and $\Delta F_{rms}$ respectively. All CPC times (seconds) are obtained from IBM RISC6000/MODEL 590 machines.

| Protein | Direct | ws = 1 p = 2 | p = 4 | p = 8 | ws = 2 p = 2 | p = 4 | p = 8 |
|---|---|---|---|---|---|---|---|
| 4 insb (292) | 0.06 | 0.08 | 0.14 | 0.42 | 0.10 | 0.14 | 0.26 |
| | | 8.740E-3 | 3.045E-3 | 4.266E-4 | 3.928E-4 | 6.222E-4 | 3.169E-5 |
| | | 2.132E-2 | 1.108E-2 | 6.284E-3 | 2.547E-4 | 7.046E-4 | 7.393E-5 |
| 1 crn (655) | 0.30 | 0.24 | 0.31 | 0.74 | 0.38 | 0.44 | 0.65 |
| | | 5.318E-4 | 4.696E-5 | 5.755E-6 | 3.488E-4 | 4.021E-6 | 1.209E-7 |
| | | 1.067E-2 | 3.035E-3 | 4.700E-4 | 1.055E-3 | 1.521E-4 | 4.575E-6 |
| 3il8 (1144) | 1.02 | 0.64 | 0.72 | 1.13 | 1.01 | 1.09 | 1.46 |
| | | 3.520E-4 | 7.194E-5 | 2.648E-5 | 6.290E-5 | 7.497E-6 | 1.624E-7 |
| | | 9.914E-3 | 3.566E-3 | 1.371E-3 | 9.698E-4 | 1.789E-4 | 9.968E-6 |
| 2rn2 (2470) | 4.98 | 1.42 | 2.55 | 8.32 | 2.50 | 3.48 | 8.24 |
| | | 1.052E-4 | 6.798E-5 | 4.934E-5 | 2.039E-4 | 1.707E-5 | 1.487E-6 |
| | | 2.507E-2 | 1.020E-2 | 3.271E-3 | 2.899E-3 | 2.327E-3 | 3.742E-5 |
| 8abp (4674) | 17.48 | 2.81 | 3.99 | 10.29 | 7.05 | 8.04 | 13.13 |
| | | 1.095E-4 | 9.061E-5 | 2.843E-5 | 1.398E-4 | 2.831E-5 | 2.229E-6 |
| | | 2.155E-2 | 8.345E-3 | 2.367E-3 | 6.933E-3 | 1.823E-3 | 2.536E-4 |
| .1prc (9513) | 76.13 | 7.32 | 14.37 | 52.52 | 13.06 | 20.26 | 60.03 |
| | | 1.720E-4 | 1.167E-4 | 1.606E-5 | 2.076E-4 | 8.478E-4 | 8.170E-6 |
| | | 3.491E-2 | 1.780E-2 | 9.655E-3 | 1.328E-2 | 4.313E-3 | 1.125E-3 |

TABLE 3

Comparison of energy conservation and associated CPU times for velocity Verlet, Constant Long-range Force Approximation (CLFA), and r-RESPA/TFMM. Here $\Delta t$ (fs) is the overall time-step (the smallest time-step is 0.5 fs for CLFA and 0.25 fs for r-RESPA/TFMM, {n} represents the combinations of separations in CLFA and r-RESPA). $T_{total}$ is the total CPU time spent in all force routines. All data are collected from 1 ps MD runs for protein ribonuclease-H IBM RIS6000/MODEL 590 machines.

| Method | {n} | $\Delta t$ | log ($\Delta E$) | R | $T_{total}$ |
|---|---|---|---|---|---|
| Verlet | — | 0.50 | −3.2861 | 0.0374 | 16776.7 |
| | — | 1.00 | −2.8746 | 0.0715 | 8363.9 |
| | — | 1.50 | −2.2127 | 0.0934 | 6401.7 |
| | — | 2.00 | −1.5436 | 0.2966 | 4218.6 |
| | — | 3.00 | —* | — | |
| CLFA | 1 | 0.50 | −3.2861 | 0.0374 | 16776.7 |
| | 2 | 1.00 | −3.0181 | 0.0574 | 9386.8 |
| | 3 | 1.50 | −2.5984 | 0.1708 | 6753.3 |
| | 4 | 2.00 | −2.3232 | 0.1885 | 5514.3 |
| | 6 | 3.00 | −2.0180 | 0.4415 | 4495.4 |
| | 8 | 4.00 | −1.8654 | 0.8730 | 3651.5 |
| RESPA/TFMM | (1,1,1,2) | 0.50 | −3.4171 | 0.0247 | 14575.2 |
| | (1,1,2,2) | 1.00 | −3.3592 | 0.0371 | 9281.6 |
| | (1,1,2,3) | 1.50 | −3.3100 | 0.0343 | 8285.4 |
| | (1,2,2,2) | 2.00 | −3.2962 | 0.0330 | 4895.0 |
| | (1,2,2,3) | 3.00 | −3.2690 | 0.0329 | 3977.9 |
| | (2,2,2,2) | 4.00 | −3.1980 | 0.0378 | 2520.7 |

*structure blows up when $\Delta t = 3.0_{fs}$ in Verlet method.

TABLE 4

Results from 0.1 ps MD runs for the protein Photosynthetic Reaction Center (9513 atoms). Detailed CPU times in various force routines are listed for the three different simulation methods, velocity Verlet, r-RESPA, r-RESPA/TFMM, for comparison. $\Delta t$ is the overall time-step, and $\{n\}$ is the representation of combinations in force separation in r-RESPA, with the smallest time-step $\delta t = 0.25$ fs.

| Method | {n} | $\Delta t$ | log ($\Delta E$) | R | $T_{stret}$ | $T_{bend}$ | $T_{tors}$ | $T_{vdN}$ | $T_{elec}$ | $T_{total}$ |
|---|---|---|---|---|---|---|---|---|---|---|
| Verlet | — | 0.25 | — | 0.0192 | 53.2 | 34.1 | 79.6 | 2916.5 | 26787.8 | 29932.4 |
| | — | 0.50 | 3.6078 | 0.0304 | 38.5 | 17.3 | 40.7 | 1485.9 | 13980.2 | 15566.3 |
| | — | 1.00 | — | 0.0523 | 19.4 | 9.1 | 22.2 | 763.3 | 6905.3 | 7692.5 |
| | — | 1.50 | 3.3346 | 0.1756 | 15.1 | 6.7 | 17.5 | 583.0 | 4553.2 | 5175.5 |
| | — | 2.00 | — | 0.3656 | 10.1 | 4.4 | 11.9 | 378.1 | 3424.6 | 3828.7 |
| | — | 3.00 | 2.7868 | — | | | | | | |
| | | | 2.0046 | | | | | | | |
| | | | 1.4190 | | | | | | | |
| | | | —* | | | | | | | |
| RESPA | (1,1,2,2) | 0.50 | — | 0.0179 | 53.3 | 34.3 | 79.5 | 2920.9 | 13935.9 | 17025.3 |
| | (2,2,2,2) | 4.00 | 3.5960 | 0.0327 | 53.0 | 17.3 | 40.8 | 380.0 | 2993.6 | 3489.1 |
| | | | 3.3734 | | | | | | | |
| RESPA/ | (1,1,1,2) | 0.50 | — | 0.0249 | 53.2 | 34.1 | 79.5 | 2907.8 | 4996.9 | 8069.4 |
| TFMM | (1,1,2,2) | 1.00 | 3.5170 | 0.0277 | 53.2 | 34.2 | 79.6 | 1462.0 | 2841.3 | 4474.4 |
| | (1,1,2,3) | 1.50 | — | 0.0248 | 54.1 | 34.8 | 80.6 | 1453.5 | 2330.4 | 3951.4 |
| | (1,2,2,2) | 2.00 | 3.4027 | 0.0303 | 53.1 | 34.3 | 79.6 | 726.1 | 1420.8 | 2314.3 |
| | (1,2,2,3) | 3.00 | — | 0.0357 | 52.6 | 33.8 | 78.9 | 719.3 | 1199.2 | 2085.0 |
| | (2,2,2,2) | 4.00 | 3.4291 | 0.0380 | 53.3 | 17.1 | 39.9 | 360.8 | 680.9 | 1154.8 |
| | (1,2,2,5) | 5.00 | — | 0.0593 | 53.1 | 34.2 | 79.6 | 703.9 | 882.4 | 1756.6 |
| | (2,2,1,5) | 5.00 | 3.3174 | 0.0729 | 53.0 | 17.2 | 39.8 | 658.5 | 858.5 | 1607.2 |
| | (2,2,5,1) | 5.00 | — | 0.1686 | 53.3 | 17.2 | 39.7 | 189.6 | 557.6 | 856.3 |
| | (2,2,2,3) | 6.00 | 3.3812 | 0.0711 | 53.2 | 17.3 | 39.8 | 371.2 | 604.1 | 1085.5 |
| | | | 3.3334 | | | | | | | |
| | | | 2.9038 | | | | | | | |
| | | | 2.6762 | | | | | | | |
| | | | 2.3520 | | | | | | | |
| | | | 2.6791 | | | | | | | |

*structure blows up when $\Delta t$-3.0 fs in Verlet method.

TABLE 5

Energy conservation of protein systems: (2rn2)/water, (8abp)/water, and lysozyme/water. The data are collected from 1.0 ps MD run of the systems for different methods. It is shown that the r-ESPA/FMM method is much faster than the standard Verlet/Ewald method for large solvated protein systems.

| Protein | Method | $(n_2,n_3,n_4)$ | $\Delta t$(fs) | log $\Delta E$ | CPU ($10^3$ sec/ps) |
|---|---|---|---|---|---|
| 2rn2/water | V-Ewald | (1,1,1) | 1 | −3.20 | 27.7 |
| (8412 atoms) | V-FMM | (1,1,1) | 1 | −3.68 | 35.0 |
| | R-FMM | (4,4,1) | 12 | −3.27 | 8.48 |
| 8abp/water | V-Ewald | (1,1,1) | 1 | −3.25 | 219 |
| (22,912 atoms) | V-FMM | (1,1,1) | 1 | −3.75 | 104 |
| | R-FMM | (4,4,1) | 12 | −3.11 | 16.4 |
| lysozyme/water | V-Ewald | (1,1,1) | 1 | −2.18 | 562.2 |
| (44,259 atoms) | V-FMM | (1,1,1) | 1 | −4.27 | 185.7 |
| | R-FMM | (4,4,1) | 12 | −3.75 | 24.1 |

What is claimed is:

1. A computer assisted method of predicting the conformational changes that a molecule will undergo comprising the following steps:

(a) selecting a first conformation of a plurality of conformations for the molecule characterized by a set of atoms, wherein each atom position is represented by a set of Cartesian coordinates;

(b) sampling a set of initial velocities of the atoms of the molecule from step (a) from a Maxwell-Boltzmann distribution function;

(c) generating a hierarchical tree structure of nested boxes to organize multipole representations of charge distributions for the molecule, wherein the multipole representations in the hierarchical box tree are calculated recursively from top to bottom of the tree, characterized by generating a multiplicity of subdivisions of a box of the tree containing the molecule of step (a);

(d) determining separately bond stretching, bond bending, torsional, and van der Waals forces associated with the molecule, the van der Waals forces being further characterized by pair distance separating atoms;

(e) determining electrostatic forces for the molecule by:
(i) recursively generating a multipole representation of each charge distribution in each nested box which contains at least one charged particle at all levels of the hierarchical tree structure starting from the top of the hierarchical tree structure from step (c);
(ii) classifying the electrostatic forces according to the distance over which they act;
(iii) determining the electrostatic forces acting upon each atom of the molecule by evaluating a force induced by a local expansion of the electric field associated with the multipoles generated in step (e)(i), wherein the level of the multipoles used is determined by the distance over which the interaction occurs as specified in step (e)(ii); and (f) propagating the molecule in time by:
(i) assigning different characteristic time steps for each class of forces specified in steps (d) and (e);
(ii) advancing both the position and the velocity for each of the atoms of the molecule from step (a) under the forces determined in steps (d) and (e), using a time-reversible factorization of a propagator which corresponds to Newton's equations of motion, wherein steps (d) and (e) are repeated after a simulation time proportional to the timestep prescribed in step (f) (i), thereby predicting the conformational changes that the molecule will undergo.

2. The computer assisted method of claim 1, wherein one or more additional conformations of the molecule are generated by repeating step (f), thereby predicting the conformational changes that the molecule will undergo over time.

3. The computer assisted method of claim 1, wherein the molecule is a biomacromolecule or a macromolecule.

4. The computer assisted method of claim 3, wherein the biomacromolecule is a protein.

5. The computer assisted method of claim 4, wherein the Cartesian coordinates for the protein are obtained from a protein data base.

6. The computer assisted method of claim 1, wherein the molecule's nested boxes are noncubic.

7. The computer assisted method of claim 1, wherein the molecule is surrounded by layers of solvent molecules and small solute molecules.

* * * * *